United States Patent
Stocki et al.

(10) Patent No.: US 12,187,805 B2
(45) Date of Patent: Jan. 7, 2025

(54) TYPE-II VNAR POLYPEPTIDES WHICH BIND HUMAN TfR-1, ENCODING NUCLEIC ACIDS THEREOF AND METHOD OF USE THEREOF

(71) Applicant: OSSIANIX, INC, Philadelphia, PA (US)

(72) Inventors: Pawel Stocki, Hertfordshire (GB); Jaroslaw Michal Szary, Cambridge (GB); Krzysztof Bartlomiej Wicher, Cambridge (GB); Laura Thei, Cambridge (GB); Julia Lynn Rutkowski, Bryn Mawr, PA (US); Mykhaylo Demydchuk, Cambridge (GB); Shu-Fen Coker, Amersham (GB)

(73) Assignee: Ossianix, Inc., Philadelphia, PA (US)

( * ) Notice: Subject to any disclaimer, the term of this patent is extended or adjusted under 35 U.S.C. 154(b) by 0 days.

(21) Appl. No.: 18/033,600

(22) PCT Filed: Nov. 9, 2021

(86) PCT No.: PCT/US2021/058661
§ 371 (c)(1),
(2) Date: Apr. 25, 2023

(87) PCT Pub. No.: WO2022/103769
PCT Pub. Date: May 19, 2022

(65) Prior Publication Data
US 2024/0026022 A1    Jan. 25, 2024

Related U.S. Application Data

(60) Provisional application No. 63/234,210, filed on Aug. 17, 2021, provisional application No. 63/112,314, filed on Nov. 11, 2020.

(51) Int. Cl.
| | |
|---|---|
| *C07K 16/28* | (2006.01) |
| *A61P 35/00* | (2006.01) |
| *C12N 15/63* | (2006.01) |
| *G01N 33/68* | (2006.01) |

(52) U.S. Cl.
CPC .......... *C07K 16/2881* (2013.01); *A61P 35/00* (2018.01); *C12N 15/63* (2013.01); *G01N 33/68* (2013.01); *C07K 2317/52* (2013.01); *C07K 2317/565* (2013.01); *C07K 2317/567* (2013.01); *C07K 2317/569* (2013.01); *C07K 2317/77* (2013.01)

(58) Field of Classification Search
CPC ............ C07K 16/2881; C07K 2317/52; C07K 2317/565; C07K 2317/567; C07K 2317/569; C07K 2317/77; A61P 35/00; C12N 15/63; G01N 33/68
See application file for complete search history.

(56) References Cited

U.S. PATENT DOCUMENTS

| | | |
|---|---|---|
| 10,479,990 B2 | 11/2019 | Hasler |
| 10,722,576 B2 | 7/2020 | Hasler |
| 11,097,010 B2 | 8/2021 | Stocki |
| 11,512,136 B2 | 11/2022 | Stocki |
| 2006/0068867 A1 | 3/2006 | White |
| 2007/0140371 A1 | 6/2007 | Horng |
| 2020/0115702 A1 | 4/2020 | Hasler |
| 2020/0316195 A1 | 10/2020 | Hasler |
| 2021/0395381 A1 | 12/2021 | Wicher |
| 2022/0031857 A1 | 2/2022 | Stocki |
| 2023/0000998 A1 | 1/2023 | Rutkowski |

FOREIGN PATENT DOCUMENTS

| | | |
|---|---|---|
| WO | 2012075037 A1 | 6/2012 |
| WO | 2015200883 A2 | 12/2015 |
| WO | 2016077840 A2 | 5/2016 |
| WO | 2018031424 A1 | 2/2018 |
| WO | 2019089395 A1 | 5/2019 |

(Continued)

OTHER PUBLICATIONS

Barelle C and Porter A (2015) Antibodies. 4:240-258. (doi:10.3390/antib4030240).*
Boado et al (2009) "Engineering and Expression of a Chimeric Transferrin Receptor Monoclonal Antibody for Blood-Brain Barrier Delivery in the Mouse," Biotechnol. Bioeng. 102:1251-8.
Couch et al. (2013) "Addressing safety liabilities of TfR bispecific antibodies that cross the blood-brain barrier." Sci. Transl. Med. 5(183): 183ra57, 1-12.

(Continued)

*Primary Examiner* — Robert S Landsman
(74) *Attorney, Agent, or Firm* — Wilson IP Law; M. Lisa Wilson

(57) ABSTRACT

The present invention relates to a high affinity, VNAR polypeptide cross reactive with primate transferrin receptors ("TfR"). This TfR-specific VNAR polypeptide was obtained by screening semisynthetic VNAR phage display libraries against recombinant human TfR-1. The VNAR polypeptides of the invention can be used alone or as a component in conjugates that target the transferrin/transferrin receptor transport system. The invention further includes use of this VNAR, its conjugates and other derivatives in diagnostic and therapeutic methods, e.g., to diagnose, treat and/or prevent a pathological condition, disorder or disease in which it is beneficial to deliver a heterologous biomolecule across the blood brain barrier or other membrane systems. This TfR-specific VNAR polypeptide can also be used to target other biological barriers such the intestines, the placenta or aberrant cells overexpressing TfR-1, for therapeutic benefit in treatment of certain cancer cells and tumors of various tissue types. Deimmunized VNAR scaffolds are also provided.

23 Claims, 11 Drawing Sheets

Specification includes a Sequence Listing.

(56) References Cited

FOREIGN PATENT DOCUMENTS

| WO | 2020056327 | A1 | 3/2020 |
| WO | 2021102276 | A1 | 5/2021 |
| WO | 2022103769 | A1 | 5/2022 |

OTHER PUBLICATIONS

Daniels et al. (2006) "The transferrin receptor part I: Biology and targeting with cytotoxic antibodies for the treatment of cancer." Clin. Immunol. 121:144-58.

Demogines et al. (2013). "Dual host virus arms races shape an essential housekeeping protein." PLoS Biol. 11(5): e1001571.

International Search Report and Written Opinion for the International Application No. PCT/US2022/040616, mailed Dec. 7, 2022, 13 pages.

International Search Report and Written Opinion for International Application No. PCT/US2021/058661, mailed Mar. 25, 2022, 12 pages.

Kariolis et al. (2020) "Brain delivery of therapeutic proteins using an Fc fragment blood-brain barrier transport vehicle in mice and monkeys." Sci. Transl. Med. 12:eaay1359.

Kleven, Mark D et al. "Transferrin Receptors TfR1 and TfR2 Bind Transferrin through Differing Mechanisms." Biochemistry vol. 57,9 (2018): 1552-1559.

Könning et al. (2017) "Camelid and shark single antibodies: structural features and therapeutic potential." Curr. Opin. Struct. Biol. 45:10-16.

Lo et al. (2017) "Effector-attenuating Substitutions That Maintain Antibody Stability and Reduce Toxicity in Mice." J. Biol. Chem. 292: 3900-3908.

Matz, Hanover, and Helen Dooley. "Shark IgNAR-derived binding domains as potential diagnostic and therapeutic agents." Developmental and comparative immunology vol. 90 (2019): 100-107.

Niewoehner et al. (2014) "Increased Brain Penetration and Potency of a Therapeutic Antibody Using a Monovalent Molecular Shuttle," Neuron 81:49-60.

Pardridge et al. (2018) "Blood-Brain Barrier Transport, Plasma Pharmacokinetics, and Neuropathology Following Chronic Treatment of the Rhesus Monkey with a Brain Penetrating Humanized Monoclonal Antibody Against the Human Transferrin Receptor." Mol. Pharm. 15: 5207-5216.

Reynisson et al. (2020) "Improved Prediction of MHC II Antigen Presentation through Integration and Motif Deconvolution of Mass Spectrometry MHC Eluted Ligand Data," J Proteome Res. 19:2304-2315.

Sehlin et al. (2020) Brain delivery of biologics using a cross-species reactive transferrin receptor 1 VNAR shuttle. FASEB J. 34(10): 13272-13283.

Silvestri et al. (2014) "The extrahepatic role of TFR2 in iron homeostasis," Front. Pharmacol. 5:93, 6 pages.

Stocki et al. (2020) "Blood-brain barrier transport using a high-affinity, brain-selective VNAR (Variable Domain of New Antigen Receptor) antibody targeting transferrin receptor 1." bioRxiv preprint, posted Jul. 20, 2020.

Stocki et al. (2021) "Blood-brain barrier transport using a high affinity, brain-selective VNAR antibody targeting transferrin receptor 1." FASEB J. 35(2): p. e21172.

White et al. (1990) "Combinations of anti-transferrin receptor monoclonal antibodies inhibit human tumor cell growth in vitro and in vivo: evidence for synergistic antiproliferative effects." Cancer Res. 50:6295-301.

White et al. (1992). "Monoclonal antibodies against defined epitopes of the human transferrin receptor cytoplasmic tail." Biochim. Biophys. Acta. 11136(1):28-34.

Yu et al. (2014) "Therapeutic bispecific antibodies cross the blood-brain barrier in nonhuman primates," Sci. Transl. Med. 3:84ra44, 10 pages.

Clarke et al., "A Single Domain Shark Antibody Targeting the Transferrin Receptor 1 Delivers a TrkB Agonist Antibody to the Brain and Provides Full Neuroprotection in a Mouse Model of Parkinson's Disease," Pharmaceutics 2022, Jun. 24, 2022, 16 pages.

Diaz et al. (1998) "Somatic hypermutation of the new antigen receptor gene (NAR) in the nurse shark does not generate the repertoire: possible role in antigen-driven reactions in the absence of germinal centers" Proc. Natl. Acad. Sci. 95:14343-14434.

Greenberg et al., "A new antigen receptor gene family that undergoes rearrangement and extensive somatic diversification in sharks," Nature, vol. 374, Mar. 9, 1995, pp. 168-173.

Kovalenko et al., "Atypical Antigen Recognition Mode of a Shark Immunoglobulin New Antigen Receptor (IgNAR) Variable Domain Characterized by Humanization and Structural Analysis," Journal of Biological Chemistry, vol. 288, No. 24, Jun. 14, 2013, pp. 17408-17419.

Streltsov et al., "Structural evidence for evolution of shark Ig new antigen receptor variable domain antibodies from a cell-surface receptor," PNAS, vol. 101, No. 34, Aug. 24, 2004, pp. 12444-12449.

Stanfield et al., "Crystal Structure of a Shark Single-Domain Antibody V Region in Complex with Lysozyme," vol. 305, Science, Sep. 17, 2004, pp. 1770-1773.

Zielonka et al., "Structural insights and biomedical potential of IgNAR scaffolds from sharks," mAbs, 7:1, 15-25, Feb. 2015, pp. 15-25.

\* cited by examiner

```
                        SEQUENCE LISTING

<160> NUMBER OF SEQ ID NOS: 9

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Asp Ser Asn Cys Ala Leu Ser Ser
1               5

<210> SEQ ID NO 2
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Val Val Gly Thr Trp Cys Met Ser Trp Arg Asp Val
1               5                   10

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Thr Asn Glu Glu Asn Ile Ser Lys Gly
1               5

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Gly Ser Lys Ser
```

<210> SEQ ID NO 5
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Val Gly Thr Trp Cys Met Ser Trp Arg Asp Val
                85                  90                  95

Tyr Gly Gly Gly Thr Ala Val Thr Val Asn Ala
            100                 105
```

<210> SEQ ID NO 6
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Ala Arg Val Asp Gln Thr Pro Gln Thr Ala Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asp Ser Gly Thr Lys
    50                  55                  60

Ser Phe Ser Leu Lys Ile Asn Asp Leu Thr Val Glu Asp Ser Gly Thr
65                  70                  75                  80

Tyr Arg Cys Asn Val Val Gly Thr Trp Cys Met Ser Trp Arg Asp Val
                85                  90                  95

Ser Gly Asp Gly Thr Val Val Thr Val Asn Ala
            100                 105
```

<210> SEQ ID NO 7
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Ala Arg Val Asp Gln Thr Pro Gln Thr Ala Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Lys Tyr Val Glu Thr Val Glu Ser Gly Ser
    50                  55                  60

Lys Ser Phe Ser Leu Lys Ile Asn Asp Leu Thr Val Glu Asp Ser Gly
65                  70                  75                  80

Thr Tyr Arg Cys Asn Val Val Gly Thr Trp Cys Met Ser Trp Arg Asp
                85                  90                  95

Val Ser Gly Asp Gly Thr Val Val Thr Val Asn Ala
            100                 105
```

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Ala Arg Val Asp Gln Thr Pro Gln Thr Ala Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asp Ser Gly Thr Lys
    50                  55                  60

Ser Phe Ser Leu Lys Ile Asn Asp Leu Thr Val Glu Asp Ser Gly Thr
65                  70                  75                  80

Tyr Arg Cys Asn Val Val Gly Thr Trp Cys Met Ser Trp Arg Asp Val
                85                  90                  95

Ser Gly Asp Gly Thr Val Val Thr Val Asn Ala
            100                 105
```

<210> SEQ ID NO 9
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Ala Arg Val Asp Gln Thr Pro Gln Thr Ala Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Lys Tyr Val Glu Thr Val Glu Ser Gly Ser
    50                  55                  60
```

-continued

```
Lys Ser Phe Ser Leu Lys Ile Asn Asp Leu Thr Val Glu Asp Ser Gly
 65              70                  75                  80

Thr Tyr Arg Cys Asn Val Val Gly Thr Trp Cys Met Ser Trp Arg Asp
                 85                  90                  95

Val Ser Gly Asp Gly Thr Val Val Thr Val Asn Ala
            100             105
```

TYPE-II VNAR POLYPEPTIDES WHICH BIND HUMAN TfR-1, ENCODING NUCLEIC ACIDS THEREOF AND METHOD OF USE THEREOF

CROSS REFERENCE TO RELATED APPLICATIONS

This application is a national stage filing under 35 U.S. § 371 of Intl. Appln. No. PCT/US2021/058661, filed Nov. 9, 2021, which claims the benefit of provisional applications U.S. Ser. No. 63/234,210, filed Aug. 17, 2021 and U.S. Ser. No. 63/112,314, filed Nov. 11, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 24, 2023, is named 9030_2001-1us4_SL.txt and is 6,733 bytes in size.

FIELD OF THE INVENTION

The present invention relates to high affinity, VNAR polypeptides cross reactive with primate transferrin receptors ("TfR"). This TfR-specific VNAR polypeptide was obtained by screening semisynthetic VNAR phage display libraries against recombinant human TfR-1. The VNAR polypeptides of the invention can be used alone or as a component in conjugates that target the transferrin/transferrin receptor transport system. The invention further includes use of the VNARs, their conjugates and other derivatives in diagnostic and therapeutic methods, e.g., to diagnose, treat and/or prevent a pathological condition, disorder or disease in which it is beneficial to deliver a heterologous biomolecule across the blood brain barrier or other membrane systems. The TfR-specific VNAR polypeptides can also be used to target other biological barriers such the intestines, the placenta or aberrant cells overexpressing TfR-1, for therapeutic benefit in treatment of certain cancer cells and tumors of various tissue types. Deimmunized VNAR scaffolds are also provided.

BACKGROUND OF THE INVENTION

Using a variety of in vitro and in vivo selection approaches, VNARs to TfR-1 have been identified that can shuttle therapeutic molecules across the brain capillary endothelium forming the impermeable blood-brain barrier "BBB") (see, e.g., WO2015/200883; WO2016/077840; WO2018/031424; WO2019/089395; WO2020/056327).

VNARs to TfR-1 that function in vivo as effective BBB shuttles have remarkably different pharmacokinetic, potency and side-effect profiles than found with monoclonal antibodies to the same receptor. Multiple VNARs have been found that are able to recognize epitopes on the external, apical domain that are conserved across species and do not interfere with endogenous ligand-receptor interactions. By contrast, monoclonal antibodies reactive with the external domain of the TfR-1 are usually highly species-specific (White 1992). This apical domain is under selective mutational pressure by species-specific pathogens that use the receptor to gain cellular entry (Demogines 2013) and is only 77% identical between the mouse and human receptor (Gerhardt 1991). Moreover, many monoclonal antibodies to the TfR-1 extracellular domain are cytotoxic, either by perturbing transferrin transport or receptor expression (White 1990; Daniels 2006).

In the approaches cited above, cross-reactive clones were found by alternately selecting VNAR libraries on mouse and human receptors presented as recombinant protein on a cell surface or by in vivo selection in mice. For example, one TfR-1 binding VNAR clone (Clone C; also known as Clone 10), selected by in vivo methods in mice, crossed the BBB when formatted as an Fc fusion and reached a concentration of 5 nM in murine whole brain tissue and is one of the most potent shuttles for TfR-1 identified to date (WO2018/031424). The next most potent clone (Clone H; WO2018/031424; also identified as Sequence 169 in that publication), reached a brain concentration of 0.7 nM.

In a murine system, both clones cross the BBB at low therapeutic doses (~2 mg/kg), are rapidly taken up into the brain (within 1 h), continue to accumulate over several days and slowly decline over the next week after a single IV injection. These profiles markedly contrast with other BBB shuttles directed to TfR-1, which are rapidly cleared by the liver (Boado 2009; Niewoehner 2014) or require very high doses (e.g., 50 mg/kg, Genentech; Yu 2014). Variants of Clone C and Clone H were prepared by a restricted random mutagenesis strategy of the VNAR CDR3 domain and several were capable of reaching higher concentrations in the brain than its corresponding parent (WO2019/089395). Nonetheless, the need remains for additional molecules that selectively deliver compounds and biomolecules (e.g., therapeutic and diagnostic agents) across membrane systems in mammalian subjects, such as into various organs, tumors or across the BBB. Moreover, it would be advantageous to have further new selective TfR-specific binding compounds, especially ones having one or more advantageous biological properties with therapeutic and/or diagnostic benefit over current anti-TfR antibodies and other regulators of iron transport systems.

The present invention thus addresses these needs for new and potent TfR-1 binders which may efficiently cross the BBB and release a therapeutic cargo in vivo, including VNARs which exhibit broader primate specificity.

SUMMARY OF THE INVENTION

The present invention relates to new, isolated Type II VNAR polypeptides comprising a VNAR domain capable of specifically binding to human TfR-1 without substantially interfering with transferrin binding to and/or transport by human TfR-1. These VNAR domains are represented by the formula, from N to C terminus, FW1-CDR1-FW2-HV2-FW2'-HV4-FW3-CDR3-FW4, wherein the CDR1 region has an amino acid sequence of DSNCALSS (SEQ ID NO. 1) and the CDR3 region has an amino acid sequence of VVGTWCMSWRDV (SEQ ID NO. 2). In some embodiments of these VNAR polypeptides, the HV2 region has an amino acid sequence of TNEENISKG (SEQ ID NO. 3). In some embodiments of these VNAR polypeptides, the HV4 region has an amino acid sequence of SGSKS (SEQ ID NO. 4). In some embodiments of these VNAR polypeptides, the HV2 region has an amino acid sequence of TNEENISKG (SEQ ID NO. 3) and the HV4 region has an amino acid sequence of SGSKS (SEQ ID NO. 4). In some embodiments, the Type II VNAR polypeptide of the inventions has a VNAR domain which comprises an amino acid sequence of ARVDQTPQTITKETGESLTINCVLRDSN-CALSSTYWYRKKSGSTNEENISKGGRY V ETVNSG-SKSFSLKINDLTVEDSGTYRC- NVVGTWCMSWRDVYGGGTAVTVNA (SEQ ID NO. 5). This VNAR domain of SEQ ID NO. 5 is also referred to herein as VNAR-txp1. The framework regions of the VNAR domains of the invention can be any natural or artificial VNAR domain framework sequence provided that it preserves the structural integrity of a Type II VNAR domain, as well as any deimmunized VNAR scaffold disclosed herein.

In some embodiments, the VNAR polypeptides of the invention are capable of uptake across the blood brain barrier.

In accordance with the invention, the VNAR polypeptides of the invention are formulated as conjugates, including but not limited to, conjugates which comprise a heterologous agent which is a diagnostic or therapeutic agent. In some embodiments, the conjugate comprises one or more of the following agents: a small molecule, a DNA, RNA, or hybrid DNA-RNA, a traceable marker such as a fluorescent or phosphorescent molecule, a radionuclide or other radioactive agent, an antibody, single chain variable domain, immunoglobulin fragment, variant or fusion, a small molecule diagnostic or therapeutic.

Further aspects of the invention are directed to nucleic acids encoding the VNAR polypeptide or conjugate, as well as vectors and host cells containing those nucleic acids and vectors.

Some aspects of the invention provide pharmaceutical compositions comprising a VNAR polypeptide of the invention or a conjugate thereof.

The instant invention also provides methods of medical treatment, including a method to administer a therapeutically-effective amount of a pharmaceutical composition of the invention to deliver a diagnostic or therapeutic agent to the brain of a mammalian subject in need thereof.

Additional methods of the invention are directed to targeting delivery of a payload to brain parenchymal tissue in a mammal by administering a VNAR polypeptide or conjugate of the invention.

Further aspects of the invention relate to kits for detecting or quantifying TfR-1 in a sample which comprises at least one VNAR polypeptide or conjugate of the invention.

Yet other aspects relate to a compound for use as a diagnostic or therapeutic agent in a subject, where the compound comprises a diagnostic or therapeutic agent operably linked to a VNAR polypeptide of the invention, and upon binding to human TfR-1 in a cell membrane, is endocytosed to thereby deliver said diagnostic or therapeutic agent across the cell membrane. In some embodiments, the operably linkage dissociates after endocytosis to release said diagnostic or therapeutic agent into said cell. In some embodiments, the cell membrane is part of the blood brain barrier or the GI tract.

Another aspect of the invention provides methods of delivering a therapeutic or diagnostic molecule across the blood brain barrier which comprises administering a VNAR polypeptide of the invention, wherein said therapeutic molecule is conjugated to said moiety, to a subject for a time and in an amount effective to treat or diagnose a CNS disease or condition.

Another aspect of the invention provides methods of delivering a therapeutic or diagnostic molecule to the gastrointestinal (GI) tract which comprises administering a VNAR polypeptide of the invention, wherein said therapeutic molecule is conjugated to said moiety, to a subject for a time and in an amount effective to treat or diagnose a GI disease or condition.

Further methods of the invention are directed to a method of treatment which comprises administering to a subject in need thereof a compound or composition comprising a VNAR polypeptide of the invention. In some embodiments, the disease or condition is ameliorated upon transport of a heterologous molecule across a cell membrane of a TfR-positive cell, wherein said heterologous molecule comprises or is associated with a VNAR polypeptide of the invention. In some embodiments, the VNAR polypeptide is internalized by a TfR in a cell membrane associated with the blood brain barrier or the gastrointestinal (GI) tract. In some embodiments, the disease or condition is a central nervous system disease or condition. In some embodiments, the disease or condition is cancer, particularly cancers wherein the cancerous cells express a higher level of TfR relative to the equivalent or similar non-cancerous cells.

Yet another aspect of the invention relates to methods of identifying, quantifying or localizing a TfR-containing biological sample or cell which comprises contacting a test sample in vitro or in vivo with a VNAR polypeptide of the invention, or a conjugate thereof, and directly or indirectly measuring the TfR-specific binding in or to said sample.

Another embodiment of the invention is directed to targeting delivery of a heterologous molecule to a TfR-expressing cell by delivering a TfR-specific conjugate of the invention to the target. Another embodiment of the invention is directed a method of increasing the oral bioavailability of a drug by associating the drug with a VNAR polypeptide of the invention.

DETAILED DESCRIPTION OF THE INVENTION

Figure 1:
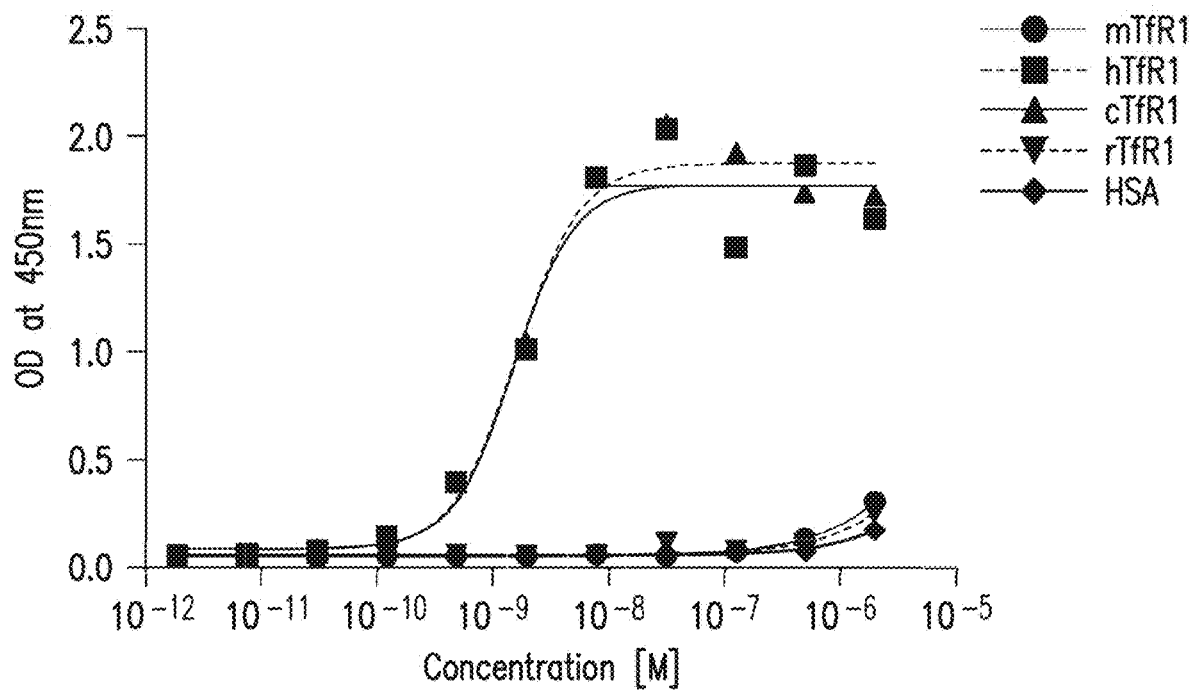
FIG. 1. Cross-species reactivity of TXP1 assessed by ELISA. Plates were coated with either mouse, human, cynomolgus or rat TfR-1. HSA was used as a negative control. Serial dilutions of TXP1 (a VNAR antibody) were added to the plate and binding was measured by end-point ELISA upon incubation with secondary anti-hFc HRP-conjugated antibodies and visualization with TMB. Absorbance was measured at 450 nm and 4-parametric non-linear regression was used to calculate EC50 values (see Table 4).

In order that the present invention may be more readily understood, certain terms are defined below. Additional definitions may be found within the detailed description of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., cows, pigs), companion animals (e.g., dogs, cats) and rodents (e.g., mice and rats).

The term "non-human mammal" means a mammal which is not a human and includes, but is not limited to, a mouse, rat, rabbit, pig, cow, sheep, goat, dog, primate, or other non-human mammals typically used in research. As used herein, "mammals" includes the foregoing non-human mammals and humans.

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically-effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

A physiologically-acceptable solution for use in an amount and for a time sufficient to effectively reduce a circulating concentration of the plurality of polypeptides is also referred to herein as a perfusate. The amount of perfusate and time of perfusion depends on the non-human mammal and can be readily determined by those of skill in the art. For example, with a mouse, using a volume of perfusate approximately 10× the blood volume of the mouse is effective at reducing the circulating concentration of polypeptides. Likewise, any volume of perfusate that reduces the circulating concentration of the plurality of polypeptides by about 10%, 25%, 50% or more (relative to the theoretical concentration of the plurality of polypeptides) being delivered is considered effective at reducing the circulating concentration of that plurality.

As used herein, the terms "VNAR antibody," "VNAR-Fc fusion," and "VNAR-Fc fusion protein" are used interchangeably, and include, but are not limited to antibodies that have a VNAR domain as their variable region and a non-IgNAR constant regions derived from the Fc fragments of IgG, IgM, IgA and IgE. In other words, the non-IgNAR constant region of a VNAR antibody include the Fc portion of conventional antibodies, whether joined by chemical linkers or joined as fusion proteins with or without amino acid linking regions. Further, VNAR antibodies can be monovalent or bivalent. For the avoidance of doubt TXP1, A06 and G12 are VNAR antibodies which have VNAR domain and an Fc domain from human IgG.

As used herein, the term "TfR," "TfR1" or "TfR-1" refers to a mammalian transferrin receptor-1 (in context as a protein or a nucleic acid), unless the context indicates that it refers specifically to human TfR-1 (see, e.g., UniProt P02786 TFR1_Human) or mouse TfR-1.

Polypeptides and Compounds Comprising a TfR Specific VNAR

The present invention relates to a new TfR-1-specific Type II VNAR polypeptide obtained by in vitro selection against recombinant human TfR-1 using semisynthetic VNAR phage display libraries.

Accordingly, one aspect of the present invention is directed to VNAR polypeptides comprising a VNAR domain capable of specifically binding to human TfR-1 without substantially interfering with transferrin binding to and/or transport by human TfR-1, wherein said VNAR domain is represented by the formula, from N to C terminus, FW1-CDR1-FW2-HV2-FW2'-HV4-FW3-CDR3-FW4,
and wherein the CDR1 region has an amino acid sequence of DSNCALSS (SEQ ID NO. 1), and the CDR3 region has an amino acid sequence of VVGTWCMSWRDV (SEQ ID NO. 2).

In some embodiments, the VNAR domain has the foregoing CDR1 and CDR3 sequences and the HV2 region has an amino acid sequence of TNEENISKG (SEQ ID NO. 3). In some embodiments, the VNAR domain has the foregoing CDR1 and CDR3 sequences and the HV4 region has an amino acid sequence of SGSKS (SEQ ID NO. 4) In further embodiments, the VNAR domain comprises a CDR1 region having amino acid sequence DSNCALSS, an HV2 region having amino acid sequence TNEENISKG (SEQ ID NO. 3), an HV4 region having amino acid sequence SGSKS (SEQ ID NO. 4), and a CDR3 region having amino acid sequence VVGTWCMSWRDV (SEQ ID NO. 2).

In some embodiments, the VNAR polypeptide is capable of binding to non-human primate TfR-1. In some embodiments, the non-human primate is a macaque (also known as a cynomolgus monkey or cynomolgus macaque). In some embodiments, the VNAR polypeptides of the invention are capable of uptake across the BBB, the GI tract or the cell membrane of a TfR-1-expressing cell.

In some embodiments, the VNAR domain comprises an amino acid sequence shown in Table 1. The first VNAR domain or VNAR polypeptide in Table 1 is also referred to herein as VNAR-txp1. When the VNAR-txp1 domain is fused to an Fc domain (see Example 2), that fusion protein is referred to herein as TXP1. The second two lines are variants of VNAR-txp1 with deimmunized scaffolds, identified and obtained and characterized as described in U.S. Ser. No. 63/234,210, filed Aug. 17, 2021. The sequences listed in Table 1 are SEQ ID NO. 5, 6 and 7, respectively.

TABLE 1

| Name | Amino Acid Sequence | Type |
| --- | --- | --- |
| VNAR-txp1 | ARVDQTPQTITKETGESLTINCVLRDSNCALSSTYWYRKKSG STNEENISKGGRYVETVNSGSKSFSLKINDLTVEDSGTYRCN VVGTWCMSWRDVYGGGTAVTVNA | II |
| VNAR-r2d1 | ARVDQTPQTATKETGESLTINCVLRDSNCALSSTYWYRKKS GSTNEENISKGGRYVETVDSGTKSFSLKINDLTVEDSGTYRC NVVGTWCMSWRDVSGDGTVVTVNA | II |
| VNAR-r2d4 | ARVDQTPQTATKETGESLTINCVLRDSNCALSSTYWYRKKS GSTNEENISKGGRKYVETVESGSKSFSLKINDLTVEDSGTYR CNVVGTWCMSWRDVSGDGTVVTVNA | II |

As used herein, a "VNAR domain" has the general structure, from N to C terminus, given by the formula FW1-CDR1-FW2-HV2-FW2'-HV4-FW3-CDR3-FW4, wherein the FWs are framework regions, CDRs are complementarity determining regions and HVs are hypervariable regions that collectively form the variable domain of a shark IgNAR ("VNAR"). The present invention is directed to Type II VNAR domains where the FW1, FW2, FW2', FW3 and FW4 regions have naturally occurring VNAR sequences or altered VNAR sequences with amino acid substitutions, insertions or deletions (typically, but not limited to, no more than 1-10 amino acids changes, insertions or deletions) provided that such alterations maintain the overall tertiary structure of the Type II VNAR, and provided that such VNAR domains have combination of CDR1, HV2, HV4, and CDR3 regions shown in Table 2. The amino acid sequences of the CDR1, HV2, HV4, and CDR3 regions of those VNAR domains are also provided in Table 2.

These VNAR scaffolds of the invention may have from 1-5 amino acid substitutions, insertions or deletions provided that such alterations maintain the overall primary and tertiary structure of the Type II VNAR and do not create a human T-cell epitope.

The VNAR domains of the invention can optionally have a His-Tag (or other convenient tag for purification purposes). In some cases, such tags are removable.

In yet another aspect of the invention, any of the VNAR polypeptides of the invention can form all or part of the variable domain of a single variable domain antibody, a bi- or tri-functional VNAR, a conventional antibody, or any fragment or fusion protein of said antibody as well as variable domains with antibody-like backbones. Such constructs can be made by methods known to those of skill in the art.

Examples of single variable domain antibodies include, but are not limited to, a shark or other cartilaginous fish

TABLE 2

Amino Acid Sequences of Specific VNAR-txp1 Regions

| Name | CDR1 | HV2 | HV4 | CDR3 |
| --- | --- | --- | --- | --- |
| VNAR-txp1 & variants | DSNCALSS (SEQ ID NO. 1) | TNEENISKG (SEQ ID NO. 3) | SGSKS (SEQ ID NO. 4) | VVGTWCMSWRDV (SEQ ID NO. 2) |

In some embodiments, the VNAR scaffold portion used with the CDR1 and CDR3 of VNAR-txp1 (and independently the HV2 and HV4 regions) comprises an amino acid sequence shown in Table 3. These VNAR scaffolds are also referred to herein as r2d1-scaffold and r2d4 scaffold. The VNAR domains derived from these scaffolds can be fused to an Fc domain (in the same manner as described in Example 2) to produce TXP1D1 and TXP1D4, respectively.

antibodies, camelid antibodies and nanobodies. Examples of conventional antibodies (and their fragments) include, but are not limited to, immunoglobins having both heavy and light chains, such as IgM's, IgA's, IgG's, IgE's, single chain Fv's, Fab fragments, or any fragment or fusion protein of such antibodies or fragments.

In preferred embodiments, any of the VNAR polypeptides of the invention can be fused to an Fc domain of a conven-

TABLE 3

Deimmunized VNAR Scaffolds

| Name | Amino Acid Sequence |
| --- | --- |
| r2d1-scaffold | ARVDQTPQTATKETGESLTINCVLR-CDR1-TYWYRKKSGSTNEENISK GGRYVETVDSGTKSFSLKINDLTVEDSGTYRCN-CDR3-SGDGTVVTVNA (SEQ ID NO. 8) |
| r2d4-scaffold | ARVDQTPQTATKETGESLTINCVLR-CDR1-TYWYRKKSGSTNEENISK GGRKYVETVESGSKSFSLKINDLTVEDSGTYRCN-CDR3-SGDGTVVTVNA (SEQ ID NO. 9) | tional antibody to form a VNAR-Fc conjugate. Such fusions can be made at the N terminus or the C terminus of the Fc domain. In some embodiments, the Fc domain is a mammalian Fc domain, including primate Fc domains. More particularly, the Fc domain is a human Fc domain (hFc), a cynomolgus macaque Fc domain (cFc) or a murine Fc domain. Most preferably the Fc domain is an hFc domain. In some embodiments, the Fc domain is from an IgG, and preferably from IgG1.

In a preferred embodiment, the VNAR-txp1 or a deimmunized variant is fused at the N-terminal end of an hFc IgG1 to form the VNAR-Fc fusion designated herein as TXP1. The hFc domain of TXP1 has attenuated effector function (AEF) and carries a series of mutations (E233P/L234V/L235A/ΔG236+A327G/A330S/P331S) (Lo 2017).

One advantage of TXP1 is that it allows for efficient brain penetration at low therapeutic doses. By comparison, uptake of a high affinity monoclonal antibody to hTfR-1 was 4 times higher by choroid plexus than the brain parenchyma in NHP (Pardridge 2018), likely due to the trapping of the antibodies in brain capillaries. The use of a low affinity, monovalent monoclonal antibody allows better brain penetration but requires the intravenous administration of large therapeutic doses (30 mg/kg) to achieve similar levels in NHP (Kariolis 2020), which is a major limitation for human translation. A high affinity bivalent VNAR antibody can achieve high brain penetration without capillary trapping, most likely due to the conformational specificity of its unique binding paratope (Konning 2017; Stocki 2020).

Non-limiting examples of antibody-like backbones that may be used according to the invention include monospecific and bispecific such as multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, $C_L$ and $C_H1$ domains, bivalent F(ab')2 fragments, Fd fragments consisting of the heavy chain and $C_H1$ domains, dimeric $C_H2$ domain fragments ($C_H2D$), Fc antigen binding domains (Fcabs), single chain Fv-$C_H3$ minibodies, bispecific minibodies, isolated complementary determining region 3 (CDR3) fragments, constrained FR3-CDR3-FR4 polypeptides, SMIP domains, and any genetically manipulated counterparts of the foregoing that retain TfR-1 binding function (see e.g., Weiner L, Cell 148: 1081-4 (2012); Ahmad Z et al., Clin Dev Immunol 2012: 980250 (2012) for reviews).

In certain embodiments, a VNAR polypeptide of the invention binds to a transferrin receptor (TfR) on the membrane of a mammalian cell and TfR specific binding mediates transport of the VNAR polypeptide and at least one associated heterologous molecule across the cell membrane. Any TfR-positive cell or cell type (i.e., one with the transferrin receptor localized at the cell membrane) may thus be used to target delivery of heterologous molecules across its membrane by association (e.g., a complex or conjugate) with a VNAR polypeptide of the invention. As described in more detail below, heterologous molecules may be selected from an enormously wide variety of agents, limited only by the target cell requiring a cell surface TfR which can internalize upon binding.

In certain embodiments of the invention, the cell membrane is part of the blood brain barrier (BBB) and TfR-mediated transport across the BBB of a heterologous molecule may be accomplished. In certain other embodiments of the invention, the cell membrane is part of the GI tract and TfR-mediated transport of a heterologous molecule may be accomplished, enabling oral drug delivery routes, especially advantageous for previously non-orally bioavailable drugs or molecules for therapeutics and/or diagnostics.

Associated heterologous molecules which may be used in conjunction with any one of the above embodiments may comprise, e.g., one or more biologically active molecules and/or imaging agents. Exemplary biologically active molecules which may be transported into a TfR-positive cell in association with a TfR-specific binding moiety of the invention include, e.g., toxins for targeted TfR-positive cell death (useful e.g., in certain hyperproliferative diseases or disorders such as cancers or aberrant proliferative conditions). Other exemplary biologically active molecules which may be transported in association with a VNAR polypeptide of the invention include, e.g., polypeptides, such as an antibody or antibody fragment; a therapeutic peptide such as a hormone, cytokine, growth factor, enzyme, antigen or antigenic peptide, transcription factor, or any functional domain thereof. Other exemplary biologically active molecules which may be transported into a TfR-positive cell in association with a VNAR polypeptide of the invention include, e.g., nucleic acid molecules, such as an oligonucleotide (e.g., single, double or more stranded RNA and/or DNA molecules, and analogs and derivatives thereof); small regulatory RNA such as shRNA, miRNA, siRNA and the like; and a plasmid or fragment thereof.

Exemplary polypeptides which may be therapeutically beneficial when administered as a heterologous molecule for TfR-mediated transport across the BBB or other TfR-containing cell membrane include but are not limited to: a brain derived neurotrophic factor (BDNF), a bone morphogenic protein (e.g., BMP-1 through BMP-7, BMP8a, BMP8b, BMP10 and BMP15), a ciliary neurotrophic factor (CNF), an epidermal growth factor (EGF), erythropoietin, a fibroblast growth factor (FGF), a glial derived neurotrophic factor (GDNF), a heptocyte growth factor, an interleukin (e.g., IL-1, IL-4, TL-6, IL-10, IL-12, IL-13, IL-15, IL-17), a nerve growth factor (NGF), a neurotrophin (e.g., NT-3 and NT-4/5), a neurturin, a neuregulin, a platelet derived growth factor (PDGF), a transforming growth factor (e.g., TGF-alpha and TGF-beta), apolipoprotein E (ApoE), a vasoactive intestinal peptide, artemin, persephin, netrin, neurotensin, GM-GSF, cardiotrophin-1, stem cell factor, midkine, pleiotrophin, a saposin, a semaporin, leukemia inhibitory factor, and the like.

Exemplary therapeutic antibodies or fragments that may be transported across the BBB or other TfR-containing cell membrane as a heterologous biologically active molecule of the invention include but are not limited to: antibodies for neurodegeneration including anti-Abeta, anti-Tau, anti-alpha-synuclein anti-Trem2, anti-C9 or f7 dipeptides, anti-TDP-43, anti-prion protein C, anti-huntingtin, anti-nogo A, anti-TRAIL (tumor necrosis factor-related apoptosis-inducing ligand); antibodies for neuro-oncology including anti-HER2, anti-EGF, anti-PDGF, anti-PD1/PDL1, anti-CTLA-4, anti-IDO, anti-LAG-3, anti-CD20, anti-CD19, anti-CD40, anti-OX40, anti-TIM3, anti-toll-like receptors; antibodies for neuroinflammation including anti-TNF, anti-CD138, anti-IL-21, anti-IL-22; antibodies to viral diseases of the brain including anti-West Nile virus, anti-Zika, anti-HIV, anti-CMVanti-HSV and the like.

Exemplary enzymes that may be transported across the BBB or other TfR-containing cell membrane as a heterologous biologically active molecule of the invention include but are not limited to: alpha-L-iduronidase, iduronate-2-sulfatase, N-acetyl-galactosamine-6-sulfatase, arylsulfatase B, acid alpha-glucosidase, tripeptidyl-peptidase 1, acid sphingomyelinase glucocerebrosidase and heparan sulfamidase.

Also included as exemplary biologically active molecules are small molecules comprising chemical moieties (such as a therapeutic small molecule drugs); carbohydrates; polysaccharides; lipids; glycolipids and the like. Exemplary embodiments of such small molecule therapeutic agents include certain cancer drugs, such as daunorubicin, doxorubicin, and other cytotoxic chemical agents including microtubule inhibitors, topoisomerase inhibitors, platins, alkylating agents, and anti-metabolites all of which may beneficially be administered across the BBB at lower overall systemic doses than by IV administration. Other small molecule therapeutic agents may include corticosteroids, NSAIDs, COX-2 inhibitors, small molecule immunomodulators, non-steroidal immunosuppressants, 5-amino salicylic acid, DMARDs, hydroxychloroquine sulfate, and penicillamine. 1-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir, among others. Small molecule therapeutic agents which may be used according to the invention also include bevacizumab, cisplatin, irinotecan, methotrexate, temozolomide, taxol and zoledronate. Certain anti-inflammatory agents may be useful biologically active molecules. Fluoxetine, for example, reportedly inhibits MMP-2, MMP-9 and MMP-12 expression associated with blood-brain barrier disruption and inflammatory reactions after spinal cord injury, which may be used according to the invention to protect blood-brain barrier and to inhibit deleterious inflammatory responses in spinal cord injury and central nervous system disease. Other non-limiting examples of therapeutic antibodies which may be beneficially transported across the BBB include anti-CD133, anti-CD137, anti-CD27, anti-VEGF, anti-EGRFvIII, anti-IL-15 and anti-IL13R.

Exemplary embodiments of an imaging agent as an associated heterologous molecule include agents that comprise at least one of a metal such as a paramagnetic metal, a radionuclide such as a radioisotope, a fluorochrome or fluorophor, an energy emitting particle, a detectable dye, and an enzyme substrate.

Further examples of biologically active molecules include small molecules, including therapeutic agents, in particular those with low blood-brain barrier permeability. Some examples of these therapeutic agents include cancer drugs, such as daunorubicin, doxorubicin, and toxic chemicals which, because of the lower dosage that can be administered by this method, can now be more safely administered. For example, a therapeutic agent can include bevacizumab, irinotecan, zoledronate, temozolomide, taxol, methotrexate, and cisplatin.

In another embodiment, the therapeutic agent can include a broad-spectrum antibiotic (e.g., cefotaxime, ceftriaxone, ampicillin and vancomycin); an antiviral agent (e.g., acyclovir); acetazolamide; carbamazepine; clonazepam; clorazepate dipotassium; diazepam; divalproex sodium; ethosuximide; felbamate; fosphenytoin sodium; gabapentin; lamotrigine; levetiracetam; lorazepam; oxcarbazepine; phenobarbital; phenytoin; phenytoin sodium; pregabalin; primidone; tiagabine hydrochloride; topiramate; trimethadione; valproic acid; zonisamide; copaxone; tysabri; novantrone; donezepil HCL; rivastigmine; galantamine; memantine; levodopa; carbidopa; parlodel, permax, requip, mirapex; Symmetrel; artane; cogentin; eldepryl; and deprenyl. Antiviral compounds are also beneficial therapeutic agents that can be delivered using a TfR-specific binding moiety of the invention, especially for cases in which the virus uses TfR transport as its route of entry into infected cells.

Numerous other examples of biologically active molecules may be used in association with a TfR-specific binding moiety of the invention, appropriate selection of which will be apparent to the skilled artisan depending on the condition, disease or disorder to be treated.

Yet other examples of a biologically active molecule which may be used according to the present invention is an antigenic peptide. Antigenic peptides may provide immunological protection when imported by cells involved in an immune response. Other examples include immunosuppressive peptides (e.g., peptides that block autoreactive T cells, such peptides being known in the art).

An imaging agent, as used herein, may be any chemical substance which may be used to provide a signal or contrast in imaging. A signal enhancing domain may be an organic molecule, metal ion, salt or chelate, a particle (e.g., iron particle), or a labeled peptide, protein, glycoprotein, polymer or liposome. For example, an imaging agent may include one or more of a radionuclide, a paramagnetic metal, a fluorochrome, a dye, and an enzyme substrate.

For x-ray imaging, the imaging agent may comprise iodinated organic molecules or chelates of heavy metal ions of atomic numbers 57 to 83. In certain embodiments, the imaging agent is $I^{125}$ labeled IgG (see, e.g., M. Sovak, ed., "Radiocontrast Agents," Springer-Verlag, pp. 23-125 (1984).

For ultrasound imaging, an imaging agent may comprise gas-filled bubbles or particles or metal chelates where the metal ions have atomic numbers 21-29, 42, 44 or 57-83. See e.g., Tyler et al., Ultrasonic Imaging, 3, pp. 323-29 (1981) and D. P. Swanson, "Enhancement Agents for Ultrasound: Fundamentals," Pharmaceuticals in Medical Imaging, pp. 682-87. (1990) for other suitable compounds.

For nuclear radiopharmaceutical imaging or radiotherapy, an imaging agent may comprise a radioactive molecule. In certain embodiments, chelates of Tc, Re, Co, Cu, Au, Ag, Pb, Bi, In and Ga may be used. In certain embodiments, chelates of Tc-99m may be used. See e.g., Rayudu G V S, Radiotracers for Medical Applications, I, pp. 201 and D. P. Swanson et al., ed., Pharmaceuticals in Medical Imaging, pp. 279-644 (1990) for other suitable compounds.

For ultraviolet/visible/infrared light imaging, an imaging agent may comprise any organic or inorganic dye or any metal chelate.

For MRI, an imaging agent may comprise a metal-ligand complex of a paramagnetic form of a metal ion with atomic numbers 21-29, 42, 44, or 57-83. In certain embodiments, the paramagnetic metal is selected from: Cr(III), Cu(II), Dy(III), Er(III) and Eu(III), Fe(III), Gd(III), Ho(III), Mn(II and III), Tb(III). A variety of chelating ligands useful as MRI agents are well known in the art.

In sum, the invention includes TfR-specific conjugate comprising a TfR-specific binding moiety of the invention operably linked to a heterologous molecule which differs in biological activity from said moiety. Such operable linkages can be a covalent or non-covalent linkage and the heterologous molecule can be a growth factor, cytokine, lymphokine, cell surface antigen or an antibody or antibody fragment which binds to any of the foregoing; a chimeric antigen receptor; a cytotoxic small molecule; a biochemical pathway agonist or antagonist; a therapeutic agent or drug; a diagnostic agent such as a fluorescent molecule or other molecular marker; or a nucleic acid molecule with targeting or other regulatory properties (e.g., silencers) or which encodes a regulatory molecule for a cell.

For the avoidance of doubt, a TfR-selective binding compound includes TfR-specific binding moieties alone, as part of antibodies (or fragments thereof as decribed herein), as part of conjugates or encoded in viral or other vectors.

Monitoring TfR Binding and Cell Internalization

TfR-binding activity (also referred to herein as "TfR bioactivity") may be determined by one or more assays described in the Examples herein, or by any other suitable method in the art, including well-known immunoassays, such as for example the ELISAs or variations thereon described in the Examples. Any other binding assay which directly or indirectly measures the binding of a VNAR polypeptide of the invention to a cell surface TfR, or alternatively, which measures the ability of the VNAR polypeptide, conjugate or compound comprising such a moiety of the invention to compete for binding to TfR in the presence of a different TfR binding compound (such as an anti-TfR antibody) such as by a competitive inhibition assay, may be used. Preferably, a selected assay measures the effect of a TfR-specific VNAR or compound comprising such a moiety on its ability to transport a heterologous molecule or biomolecule across the membrane of a TfR-positive cell. In certain embodiments, the TfR-positive cell is one which transports a heterologous molecule across the blood brain barrier (BBB). In certain embodiments, the TfR-positive cell is one which transports a heterologous molecule across cells of the gastrointestinal tract. In certain embodiments, binding of the TfR binding moiety to TfR is measured by monitoring internalization of a VNAR polypeptide of the invention into TfR-positive cells or cell type. In vivo assays of TfR bioactivity include, but are not limited to those described in the Examples herein.

Other test systems to assess TfR binding and functional activity include, for example: Surface plasmon resonance to determine affinity and off-rates; using radiolabeled or fluorescent tagged molecule or GFP fusion proteins in in vitro or in vivo animal studies including binding and internalization in tumor cell lines, immortalized endothelial cell lines or primary cells expressing TfR; in vitro transcytosis in capillary endothelial cells and cells lines; and permeability assay using Caco-2 and MDCK epithelial cell lines; in situ perfusion models and immunohistochemical or immunofluorescent staining of tissue sections; optical or PET animal imaging; standard PK and tissue distribution assays; and measuring one or more biological effects of a heterologous molecule (drug cargo or payload) in normal animals or disease animal models.

Therapeutic versions of compounds with TfR-specific binding moieties of the invention include other molecular configurations, e.g., a VNAR monomer fused to stabilizing heterologous peptide regions, e.g., the Fc domain of an IgG or other immunoglobulin molecule, which may be expressed and then further purified as multimers, such as covalent dimmers, allowing the activity of certain such therapeutic molecules to have even greater potency, preferably by at least 2-10 fold higher potencies and different binding affinities to TfR-1. Any of the antibody or antibody-like structures contemplated by the invention can be used as therapeutics Pharmaceutically acceptable salts or solvates of any of the TfR-specific binding compounds of the invention are likewise within the scope of the present invention. As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type N(R1)(R2)(R3)(R4)+, wherein R1, R2, R3 and R4 independently will typically designate hydrogen, optionally substituted $C_{1-6}$-alkyl groups or optionally substituted $C_{2-6}$-alkenyl groups. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977).

The term "solvate" in the context of the present invention refers to a complex of defined stoichiometry formed between a solute (in casu, a peptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

In each of the sequences described above, and in each sequence described herein, a C-terminal "—OH" moiety may be substituted for a C-terminal "—NH2" moiety, and vice-versa.

Each of the specific compounds of the invention (e.g., TfR binding moieties, TfR antagonist peptides and compounds), and pharmaceutically acceptable salts and solvates thereof, constitutes an individual embodiment of the invention.

Conjugates

VNAR polypeptides of the invention may optionally be conjugated (e.g., using linkers such as chemical linkers and/or linker peptides which are not usually associated with the domains being associated) to one or more additional agents which may include therapeutic and/or diagnostic agents. Such agents include but are not limited to chemotherapeutics such as cytostatic drugs, cytotoxins, radioisotopes, chelators, enzymes, nucleases, nucleic acids such as DNA, RNA or mixed nucleic acid oligonucleotides, including siRNAs, shRNAs, microRNAs, aptamers and the like; immunomodulators such as therapeutic antibodies, antibody and antibody-like fragments, inflammatory and anti-inflammatory cytokines, anti-inflammatory agents, radiotherapeutics, photoactive agents, diagnostic markers and the like. In certain embodiments, the pharmaceutically active moieties of the invention comprise at least one scFv molecule that is operably linked via a linker peptide to the C-terminus and/or N-terminus of an Fc region.

In certain embodiments, a compound of the invention comprising a TfR-specific binding moiety is multispecific, i.e., has at least one binding site that binds to a first molecule or epitope of a molecule (e.g., human TfR-1) and one or more other binding sites that bind to at least one heterologous molecule or to an epitope of either TfR-1 or another molecule. Multispecific binding molecules of the invention may comprise at least two binding sites, three binding sites, four binding sites or more. In certain embodiments, at least two binding site of a multispecific binding molecule of the invention are capable of transporting a linked molecule across the BBB.

The invention thus further provides methods of making derivatives of the TfR specific VNARs of the invention using biochemical engineering techniques well known to those of skill in the art. Such derivatives include, inter alia, multivalent or multispecific molecules comprising a VNAR polypeptides of the invention, including immunoconjugates. A large body of art is available relating to how to make and use antibody drug conjugates. Such knowledge and skill in the art may be adapted for use with the TfR specific VNARs and TfR selective binding compounds of the invention. See, e.g., WO2007/140371; WO2006/068867 specific to TfR; methods relating to making and/or using different ligand conjugates may be applied. In certain embodiments, the TfR selective binding moieties and TfR selective binding compounds of the present invention include covalently modified and conjugated polypeptides forms of the polypeptides (e.g., immunoadhesins, radiolabeled or fluorescently labeled compounds, and the like). Methods for peptide conjugation and for labeling polypeptides and conjugating molecules are well known in the art.

Nucleic Acid Sequences that Encode a TfR Selective Binding Moiety

In one aspect, the invention provides an isolated nucleic acid which encodes a VNAR polypeptide, conjugate or compound of the invention, or a fragment or derivative thereof. The invention also provides an isolated nucleic acid molecule comprising a sequence that hybridizes under stringent conditions to a nucleic acid sequence which encodes a VNAR polypeptide or compound of the invention, or a fragment or derivative thereof, or the antisense or complement of any such sequence.

In another aspect, the invention provides an isolated nucleic acid molecule encoding a fusion protein comprising at least two segments, wherein one of the segments comprises a VNAR domain of the invention. In certain embodiments, a second segment comprises a heterologous signal polypeptide, a heterologous binding moiety, an immunoglobulin fragment such as a Fc domain, or a detectable marker.

One aspect of the invention provides isolated nucleic acid molecules that encode VNAR polypeptides or biologically active portions thereof. Also included are nucleic acid fragments sufficient for use as hybridization probes to identify TfR binding moiety encoding nucleic acids and fragments for use as polymerase chain reaction (PCR) primers for the amplification or mutation of nucleic acid molecules encoding VNAR polypeptides of the invention.

As used herein, the term "nucleic acid molecule" is intended to include DNA molecules, RNA molecules (e.g., mRNA, shRNA, siRNA, microRNA), analogs of the DNA or RNA generated using nucleotide analogs, and derivatives, fragments and homologs thereof. The nucleic acid molecules of the invention may be single-, double-, or triple-stranded. A nucleic acid molecule of the present invention may be isolated using sequence information provided herein and well known molecular biological techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., CURRENT PROTOCOLS IN MOLECULAR BIOLOGY, John Wiley & Sons, New York, N.Y., 1993).

A nucleic acid molecule of the invention may be amplified using any form of nucleic acid template and appropriate oligonucleotide primers according to standard PCR amplification techniques. Amplified nucleic acid may be cloned into an appropriate vector and characterized, e.g., by restriction analysis or DNA sequencing. Furthermore, oligonucleotides corresponding to nucleotide sequences that encode a TfR selective binding moiety or compound of the invention may be prepared by standard synthetic techniques, e.g., using an automated DNA synthesizer.

The term "oligonucleotide" as used herein refers to a series of covalently linked nucleotide (or nucleoside residues, including ribonucleoside or deoxyribonucleoside residues) wherein the oligonucleotide has a sufficient number of nucleotide bases to be used in a PCR reaction. Oligonucleotides comprise portions of a nucleic acid sequence having at least about 10 nucleotides and as many as 50 nucleotides, preferably about 15 nucleotides to 30 nucleotides. Oligonucleotides may be chemically synthesized and may be used as probes. A short oligonucleotide sequence may be used to amplify, confirm, or reveal the presence of an identical, similar or complementary DNA or RNA in a particular cell or tissue.

Derivatives or analogs of the nucleic acid molecules (or proteins) of the invention include, inter alia, nucleic acid (or polypeptide) molecules having regions that are substantially homologous to the nucleic acid molecules or proteins of the invention, e.g., by at least about 45%, 50%, 70%, 80%, 95%, 98%, or even 99% identity (with a preferred identity of 80-99%) over a nucleic acid or amino acid sequence of the same size or when compared to an aligned sequence in which the alignment is done by a computer homology program known in the art. A percent identity for any candidate nucleic acid or polypeptide relative to a reference nucleic acid or polypeptide may be determined by aligning a reference sequence to one or more test sequences using, for example, the computer program ClustalW (version 1.83, default parameters), which enable nucleic acid or polypeptide sequence alignments across their entire lengths (global alignment) or across a specified length. The number of identical matches in such a ClustalW alignment is divided by the length of the reference sequence and multiplied by 100.

Also included are nucleic acid molecules capable of hybridizing to the complement of a sequence encoding the proteins of the invention under stringent or moderately stringent conditions. See e.g. Ausubel, et al., CURRENT PROTOCOLS IN MOLECULAR BIOLOGY, John Wiley & Sons, New York, N.Y., 1993, and below. An exemplary program is the GAP program (Wisconsin Sequence Analysis Package, Version 8 for UNIX, Genetics Computer Group, University Research Park, Madison, Wis.) using the default settings, which uses the algorithm of Smith and Waterman (1981) Adv. Appl. Math. 2:482489). Derivatives and analogs may be full length or other than full length, if the derivative or analog contains a modified nucleic acid or amino acid, as described below.

Stringent conditions are known to those skilled in the art and may be found in CURRENT PROTOCOLS IN MOLECULAR BIOLOGY, John Wiley & Sons, N.Y. (1989), 6.3.1-6.3.6. In certain embodiments, stringent conditions typically permit sequences at least about 65%, 70%, 75%, 85%, 90%, 95%, 98%, or 99% homologous to each other to remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. The term "stringent hybridization conditions" as used herein refers to conditions under which a nucleic acid probe, primer or oligonucleotide will hybridize to its target sequence, but only negligibly or not at all to other nucleic acid sequences. Stringent conditions are sequence- and length-dependent, and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide.

Methods of Producing TfR-Specific VNAR Polypeptides and Corresponding Compounds

The compounds of the invention may be manufactured by standard synthetic methods, by use of recombinant expression systems, or by any other suitable method. Thus, the compounds may be synthesized in a number of ways, including, e.g., methods comprising: (1) synthesizing the polypeptide or polypeptide component of a VNAR polypeptide of the invention using standard solid-phase or liquid-phase methodology, either stepwise or by fragment assembly, and isolating and purifying the final peptide compound product; (2) expressing a nucleic acid construct that encodes the polypeptide or polypeptide component of a VNAR polypeptide of the invention in a host cell and recovering the expression product from the host cell or host cell culture; or (3) cell-free in vitro expression of a nucleic acid construct encoding the polypeptide or polypeptide component of a VNAR polypeptide of the invention, and recovering the expression product; or by any combination of the methods of (1), (2) or (3) to obtain fragments of the peptide component, subsequently joining (e.g., ligating) the fragments to obtain the peptide component, and recovering the peptide component.

It may be preferable to synthesize a polypeptide or polypeptide component of a VNAR polypeptide of the invention by means of solid-phase or liquid-phase peptide synthesis. Compounds of the invention may suitably be manufactured by standard synthetic methods. Thus, peptides may be synthesized by, e.g., methods comprising synthesizing the peptide by standard solid-phase or liquid-phase methodology, either stepwise or by fragment assembly, and isolating and purifying the final peptide product. In this context, reference may be made to WO1998/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a VNAR polypeptide of the invention according to above recited methods; a nucleic acid molecule encoding part or all of such polypeptides, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

VNAR polypeptides of the invention may be prepared using recombinant techniques well known in the art. In general, methods for producing polypeptides by culturing host cells transformed or transfected with a vector comprising the encoding nucleic acid and recovering the polypeptide from cell culture are described in, e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995).

A nucleic acid encoding a desired polypeptide may be inserted into a replication vector for further cloning (amplification) of the DNA or for expression of the nucleic acid into RNA and protein. A multitude of cloning and expression vectors are publicly available.

Expression vectors capable of directing transient or stable expression of genes to which they are operably linked are well known in the art. The vector components generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

Any suitable host cell may be used to produce VNAR polypeptides of the invention. Host cells may be cells stably or transiently transfected, transformed, transduced or infected with one or more expression vectors which drive expression of a polypeptide of the invention. Suitable host cells for cloning or expressing nucleic acids of the invention include prokaryote, yeast, or higher eukaryote cells. Eukaryotic microbes such as filamentous fungi yeast, *Arabidopsis*, and other plant and animal eukaryotic host cells that may be grown in liquid culture are suitable cloning or expression hosts for vectors. Suitable host cells for the expression of glycosylated polypeptides may also be derived from multicellular organisms.

Creation and isolation of host cell lines producing a VNAR polypeptide, conjugate or compound of the invention can be accomplished using standard techniques known in the art. Mammalian cells are preferred host cells for expression of peptides. Particularly useful mammalian cells include, inter alia, HEK 293, NSO, DG-44, and CHO cells, but any other suitable host cell may be used according to the invention. Preferably, the VNAR polypeptides, conjugates or compounds are secreted into the medium in which the host cells are cultured, from which the VNAR polypeptides, conjugates or compounds may be recovered or purified.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed. Such procedures include, inter alia, fractionation (e.g., size separation by gel filtration or charge separation by ion-exchange column); ethanol precipitation; Protein A Sepharose columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a TfR-specific binding moiety, conjugate or compound of the invention.

Methods of Detection

In certain embodiments, the VNAR polypeptides of the invention may be used to detect and quantify levels of TfR, or cells that express TfR. This can be achieved, for example, by contacting a test sample (such as an in vitro sample) and a control sample with a VNAR polypeptides of the invention, or a conjugate or compound comprising it, under conditions which permit formation of a complex between the compound and TfR, or between TfR and an anti-TfR antibody, or both. Any bound TfR complexes are detected and/or quantified in TfR specific VNAR containing samples and control samples.

Accordingly, the invention further provides methods for detecting the presence of TfR or TfR antibodies in a sample, or measuring the amount of either of the foregoing, comprising contacting the sample, and preferably a control sample, with a VNAR polypeptide of the invention under conditions that permit complex formation between the TfR-binding VNAR and TfR, e.g., human TfR. Formation or inhibition of formation of a TfR-binding VNAR/TfR complex is then detected and/or quantified. A variety of tests can be designed based on features of binding or competition for binding. For example, the presence of TfR in a test sample may be detected directly, or may be detected and quantified based on the ability to compete for binding of TfR by a TfR-binding VNAR polypeptide, conjugate or compound. In general, the difference in complex formation between a test sample and a control sample is indicative of a binding interaction.

Methods of Treatment Using TfR Binding Moieties and Compositions

The present invention provides VNAR polypeptides that bind TfR and/or TfR specific binding compounds for use, alone or in combination with one or more additional therapeutic agents in a pharmaceutical composition, for treatment or prophylaxis of conditions, diseases and disorders responsive to modulation (such as inhibiting or blocking) of the interaction between TfR and its in vivo ligands.

In certain embodiments, a VNAR polypeptide or a conjugate or drug delivery vehicle comprising such a polypeptide is administered in combination with at least one additional agent that mediates blood-brain barrier transport, such as an agent comprising a receptor binding domain of an apolipoprotein such as a receptor binding domain of ApoA, ApoB, ApoC, ApoD, ApoE, ApoE2, ApoE3 or ApoE4, and any combination thereof. Any one of a number of other molecules which mediate transport of heterologous molecules across the blood brain barrier may be used in combination with the TfR specific binding VNARs comprising agents of the invention, including, e.g., IgG, YY (PYY), neuropeptide Y (NPY), corticotropin releasing factor (CRF), and urocortin. Certain viral glycoproteins (e.g., rabies virus glycoprotein (RVG) peptide) and antibodies and antibody fragments may also be used in this regard.

Combination therapies may include co-administration of agents or alternate administrations which result in a combination therapy within the patient based on duration of the therapeutic agent(s) or their biological effects in the patient.

In certain embodiments, a therapeutic agent transported across the BBB in association with a VNAR polypeptide of the invention is effective in treating a brain or CNS disease, condition, injury or disorder, such as, for example, neurodegenerative diseases, neuronal injury, stroke, genetic disorders, psychiatric disorders, developmental disorders, inflammation, infection or damage, and brain cancers, spinal cord injury (SCI) and traumatic brain injury (TBI). In certain embodiments, a brain disorder is selected from epilepsy, meningitis, encephalitis including HIV Encephalitis, progressive multifocal leukoencephalopathy, neuromyelitis optica, multiple sclerosis, late-stage neurological trypanosomiasis, amyotrophic lateral sclerosis (ALS), progressive bulbar palsy (PBP), primary lateral sclerosis (PLS), progressive muscular atrophy (PMA), Alzheimer's disease, Parkinson's disease, Huntington's disease, De Vivo disease, and any type of tumor, cancer or hyperproliferative disease in the brain or CNS.

In certain embodiments, a therapeutic agent transported across a hTfR-1-containing membrane in association with a VNAR polypeptide or conjugate of the invention is effective in treating a condition, disease or disorder associated with the GI tract or one which will otherwise benefit from drug delivery across an epithelial membrane of the gut mediated by hTfR-1 transport.

The invention in certain embodiments provides methods of treatment or prevention of a TfR associated disorder, the method comprising the step of administering to a subject (e.g., a patient) in need thereof a therapeutically effective amount of the TfR specific binding compound or pharmaceutical composition comprising a TfR binding compound of the invention, as described herein. As used herein, an "effective amount," a "therapeutically effective amount" or an "effective dose" is an amount of a composition (e.g., a therapeutic composition or agent) that produces at least one desired therapeutic effect in a subject, such as preventing or treating a target condition or beneficially alleviating a symptom associated with the condition.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, P A, 2005.

Additionally, for some embodiments, specificity for TfR-1 is an important feature for a BBB carrier because off target binding to TfR2 could have undesirable safety and/or PK consequences. The expression of TFR2 is restricted to hepatocytes and erythroid precursors (Silvestri 2014). Interference with transferrin binding to TfR2, which is a component of the erythropoietin receptor complex, could disrupt normal erythropoiesis (Forejtnikovà 2010). Additionally, high levels of TfR2 expressed in the liver may be responsible for the rapid clearance and short half-life of some cross-reacting TfR antibodies (Boado 2009). VNAR antibodies to TfR-1 are highly specific and exhibit the same long half-life as IgG.

Pharmaceutical Compositions

The present invention further provides pharmaceutical compositions comprising a VNAR polypeptide of the invention or compound, or a pharmaceutically acceptable salt or solvate thereof, according to the invention, together with a pharmaceutically acceptable carrier, excipient or vehicle.

Accordingly, the present invention further provides a pharmaceutical composition comprising a VNAR polypeptide of the invention, conjugate or compound comprising a TfR-specific VNAR domain, as well as variant and derivative compounds thereof. Certain embodiments of the pharmaceutical compositions of the invention are described in further detail below.

The present invention also provides pharmaceutical compositions comprising a VNAR polypeptide or conjugate of the invention or a TfR-specific binding compound for use in treating, ameliorating or preventing one or more diseases, conditions, disorders or symptoms relating to B cells and immunoglobulin production, as described in further detail below. Each such disease, condition, disorder or symptom is envisioned to be a separate embodiment with respect to uses of a pharmaceutical composition according to the invention.

Formulations, Administration and Dosing

VNAR polypeptides, conjugates or compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a polypeptide, conjugate or compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically-acceptable salt" refers to the salt of the compounds. As used herein a pharmaceutically-acceptable salt retains qualitatively a desired biological activity of the parent compound without imparting any undesired effects relative to the compound. Salts include pharmaceutically acceptable salts such as acid addition salts and basic salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and di-carboxylic acids, phenyl-substituted alkanoic acids, hydroxy alkanoic acids, aromatic acids, aliphatic and aromatic sulfonic acids and the like. Examples of basic salts include salts where the cation is selected from alkali metals, such as sodium and potassium, alkaline earth metals such as calcium and magnesium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl, and more specifically, the organic amines, such as N, N'-dibenzylethylenediamine, N-methylglucamine, chloroprocaine, choline, diethanolamine, ethylenediamine, procaine and the like. Other examples of pharmaceutically acceptable salts are described in "Remington's Pharmaceutical Sciences", 17th edition. Ed. Alfonso R. Gennaro (Ed.), Mark Publishing Company, Easton, PA, U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

An acceptable route of administration may refer to any administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

In another aspect, the present invention provides a composition, e.g., a pharmaceutical composition, comprising one or a combination of different TfR specific VNAR polypeptides of the invention, or an ester, salt or amide of any of the foregoing, and at least one pharmaceutically acceptable carrier. Such compositions may include one or more different TfR specific moieties or compounds in combination to produce an immunoconjugate or multi-specific molecule comprising at least one VNAR polypeptide of the invention specific for hTfR. For example, a pharmaceutical composition of the invention may comprise a combination of hTfR specific binders which bind to different epitopes of TfR or which otherwise have complementary biological activities.

Pharmaceutical compositions of the invention may be administered alone or in combination with one or more other therapeutic or diagnostic agents. A combination therapy may include a VNAR polypeptide of the present invention combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

As used herein, "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the VNAR polypeptide-comprising compound or component may be coated in a material or materials intended to protect the compound from the action of acids and other natural inactivating conditions to which the active TfR binding VNAR moiety may encounter when administered to a subject by a particular route of administration.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants.

TfR selective binding moieties and compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

Exemplary pharmaceutically acceptable carriers include sterile aqueous solutions or dispersions and sterile powders for the extemporaneous preparation of sterile injectable solutions or dispersion. Such media and reagents for pharmaceutically active substances are known in the art. The pharmaceutical compositions of the invention may include any conventional media or agent unless any is incompatible with the active TfR specific binding compound. Supplementary active compounds may further be incorporated into the compositions.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a VNAR polypeptide (or a TfR binding compound comprising such a polypeptide) in the required amount in an appropriate solvent with one or a combination of ingredients described above, as required, followed by sterilization microfiltration. Dispersions may be prepared by incorporating the active compound into a sterile vehicle that contains dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a TfR selective binding moiety or composition of the invention is administered by, e.g., intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of active ingredient which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens may be adjusted to provide the optimum desired response (e.g., a therapeutic response). For example, a single bolus may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect in association with the required pharmaceutical carrier. The specification for the dosage unit forms of the invention depend on the specific characteristics of the active compound and the particular therapeutic effect(s) to be achieved, taking into consideration and the treatment and sensitivity of any individual patient.

For administration of a VNAR polypeptide, conjugate thereof or compound therewith, the dosage range will generally be from about 0.0001 to 100 mg/kg, and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular subject, e.g., patient. TfR specific binding VNARS, conjugates and compounds will typically be administered on multiple occasions. Intervals between single dosages can be, for example, 2-5 days, weekly, monthly, every two or three months, every six months, or yearly. Intervals between administrations can also be irregular, based on regulating blood levels of TfR specific binding compound to the target TfR ligand in the subject or patient. In some methods, dosage is adjusted to achieve a plasma antagonist concentration of about 1-1000 µg/ml and in some methods about 25-300 µg/ml. Dosage regimens for a TfR specific binding compound of the invention include intravenous administration of 1 mg/kg body weight or 3 mg/kg body weight with the compound administered every two to four weeks for six dosages, then every three months at 3 mg/kg body weight or 1 mg/kg body weight.

In certain embodiments, two or more TfR specific binding compounds with different binding properties may be administered simultaneously or sequentially, in which case the dosage of each administered compound may be adjusted to fall within the ranges described herein.

In certain embodiments, a TfR specific binding compound of the invention may be administered as a sustained release formulation, in which case less frequent administration is required. Dosage and frequency vary depending on the half-life of the TfR specific binding compound in the subject or patient. The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of the TfR specific binding compound alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular TfR specific binding compound or composition employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject or patient being treated, and similar factors well known in the medical arts.

Administration of a "therapeutically effective dosage" of a TfR-binding compound of the invention may result in a decrease in severity of disease symptoms, an increase in frequency and duration of disease symptom-free periods, or a prevention of impairment or disability due to the disease affliction.

A VNAR polypeptide or composition of the present invention may be administered via one or more routes of administration, using one or more of a variety of methods known in the art. As will be appreciated by the skilled worker, the route and/or mode of administration will vary depending upon the desired results. Routes of administration for VNAR polypeptides, compounds or compositions of the invention include, e.g., intravenous, intramuscular, intradermal, intraperitoneal, subcutaneous, spinal or other parenteral routes of administration, for example by injection or infusion. The phrase "parenteral administration" as used herein refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

In other embodiments, a VNAR polypeptide, compound or composition of the invention may be administered by a non-parenteral route, such as a topical, epidermal or mucosal route of administration, for example, intranasally, orally, vaginally, rectally, sublingually or topically.

As described elsewhere herein, an active TfR specific binding compound may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compounds or compositions of the invention may be administered with one or more of a variety of medical devices known in the art. For example, in one embodiment, a therapeutic TfR specific binding composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the TfR specific binding compound or composition of the invention may be formulated to ensure a desired distribution in vivo. For example, the blood-brain barrier (BBB) excludes many highly hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 and the like.

Kits for Detecting or Quantifying TfR in a Sample

Also within the scope of the invention are kits comprising at least one VNAR polypeptide, conjugate or TfR specific binding compound or composition of the invention, and optionally, instructions for use. Kits may be useful for quantifying TfR or TfR specific antibodies in a sample, or may be useful for detection of TfR, such as in diagnostics methods. The kit may further or alternatively comprise at least one nucleic acid encoding a VNAR polypeptide of the invention. A kit of the invention may optionally comprise at least one additional reagent (e.g., standards, markers and the like). Kits typically include a label indicating the intended use of the contents of the kit. The kit may further comprise reagents and other tools for measuring TfR in a sample or in a subject, or for diagnosing whether a patient belongs to a group that responds to a TfR-specific binding compound which makes use of a compound, composition or related method of the invention as described herein.

Delivery Devices and Further Kits

In certain embodiments, the invention relates to a device comprising one or more TfR specific binding compounds of the invention, or pharmaceutically acceptable salts or solvates thereof, for delivery to a subject. Thus, one or more compounds of the invention or pharmaceutically acceptable salts or solvates thereof can be administered to a patient in accordance with the present invention via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising one or more peptides, or pharmaceutically acceptable salts or solvates thereof, of the invention. In other embodiments, the kit comprises one or more pharmaceutical compositions comprising one or more peptides or pharmaceutically acceptable salts or solvates thereof. In certain embodiments, the kit further comprises packaging and/or instructions for use.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

EXAMPLES

The examples presented herein represent certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

Example 1. Library Preparation and VNAR Selection

The semi-synthetic Type I and Type II VNAR phage libraries (OSX-4 and OSX-3, respectively), were designed to exclude human T-cell epitopes (described in WO2015/

200883). Phage libraries were produced in super-infected *E. coli* strain TG1 cultures and PEG/NaCl precipitated. Three rounds of in vitro selections were performed on in-house purified recombinant human TfR-1 ectodomain that was biotinylated using Sulfo-NHS-Biotin EZ-Link™ kit (Thermo Fisher) as described in WO2018/031424 (Example 1). The libraries were first deselected on streptavidin coupled Dynabeads® (Thermo Fisher), which were then used to pull down phages bound to hTfR-1. The beads were washed, bound phages were eluted in 100 nM triethylamine and used to infect TG1 after adjusting to neutral pH. The output titer was calculated by counting antibiotic-resistant colonies, and the culture super-infected with M13KO7 helper phage to produce phages for subsequent rounds of selection.

Novel VNAR binders to hTfR-1 were identified by phage ELISA and Sanger sequencing.

Example 2. Production and Purification of Human Fc Fusion VNAR Antibody, TXP1

Selected VNARs were synthesized and cloned into an expression vector containing human IgG1 Fc domain. The final VNAR antibody constructs were bivalent molecules with the VNAR domain fused to the N-terminus of a hFc domain with effector mutations (Lo 2017).

The VNAR-hFc formats were produced with VNARs at N-terminal end of hFc IgG1. A hFc domain with attenuated effector function (AEF) that carries a series of mutations (E233P/L234V/L235A/AG236+A327G/A330S/P331S) (Lo 2017) was used for all constructs. The Exp293F expression system (Thermo Fisher) was used for protein production following the manufacturer's manual. After 5 days growth, the cells were centrifuged at 2,000 rpm for 10 min. Supernatants were filtered using 0.22 µm membranes and loaded onto HiTrap® MabSelect SuRe® column (GE Healthcare) pre-equilibrated against PBS, pH 7.4. Protein A affinity bound proteins were eluted with 0.1 M glycine, pH 3.5 and the buffer exchanged to PBS, pH 7.4 using HiPrep 26/10 Desalting column (GE Healthcare). Protein purity was assessed by analytical size exclusion chromatography (SEC) and sodium dodecyl sulfate polyacrylamide gel electrophoresis (SDS-PAGE). Endotoxins level test was carried out using Endotoxin LAL assay with Endosafe nexgen-PTS kit at 5-0.05 EU/ml sensitivity range.

Purified VNAR-hFc antibodies were extensively characterized and the VNAR-hFc named TXP1 was further characterized (Table 1 and 2).

Example 3. TXP1 Cross Reactivity and Binding Kinetics

TfR-1 binding ELISA. Nunc MaxiSorp plates were coated with 100 µl of 1 µg/ml of in-house purified recombinant human, mouse, rat and cynomolgus TfR-1 and incubated at 4° C. overnight. Plates were incubated with blocking buffer (2.5% non-fat dry milk in PBST) for 1 h at RT. Serially-diluted TXP1 was mixed with non-fat dry milk in PBST to a final concentration of 2.5% and incubated for 30 min. Blocked TXP1 solutions (100 µl) were transferred to the blocked plates and incubated for 1 hr. Plates were washed with PBST and incubated with anti-hFc HRP-conjugated antibody diluted 1:5,000 (Sigma) in blocking buffer for 30 min. Plates were washed and developed with SureBlue™ TMB substrate, the reaction stopped with 1% HCl and absorbance measured at 450 nm.

TfR-1 binding ELISA. Nunc® MaxiSorp™ plates were coated with 100 µl of 1 µg/ml of in-house purified recombinant human, mouse, rat and cynomolgus TfR-1 and incubated at 4° C. overnight. Plates were incubated with blocking buffer (2.5% non-fat dry milk in PBST) for 1 h at RT. Serially-diluted TXP1 was mixed with non-fat dry milk in PBST to a final concentration of 2.5% and incubated for 30 min. Blocked TXP1 solutions (100 µl) were transferred to the blocked plates and incubated for 1 hr. Plates were washed with PBST and incubated with anti-hFc HRP-conjugated antibody diluted 1:5,000 (Sigma) in blocking buffer for 30 min. Plates were washed and developed with SureBlue™ TMB substrate, the reaction stopped with 1% HCl and absorbance measured at 450 nm.

Binding kinetics. Binding kinetics of TXP1 and A06 VNAR antibodies were determined by surface plasmon resonance (SPR) using a Biacore® T200 analyzer (GE Healthcare). A His-capture kit (GE Healthcare) was used to immobilize anti-His antibodies on CM5 chips (as recommended by the manufacturer). His-tagged recombinant cynomolgus and human TfR-1 in 0.1% BSA in HBS-EP+ buffer (GE Healthcare) was captured at flow rate 10 µl/min. Analyte binding was measured using the single cycle kinetic SPR method on a Biacore® T200 analyzer. Analytes were injected at increasing concentrations (0.98, 3.9, 15.6, 62.5 and 250 nM) in HBS-EP+ at flow rate 30 µl/min. A flow cell without TfR-1 captured served as a reference. The chips were regenerated in 10 mM glycine-HCl, pH 1.5. Sensorgrams were fitted using 1:1 binding model and kinetic constants determined using Biacore® T200 Evaluation software (GE Healthcare). Association and dissociation were measured for 360 s and 1500 s respectively, with flow rate at 30 ml/min.

Results. Binding of TXP1 to recombinant human, cynomolgus, mouse and rat TfR-1 by ELISA showed cross-species reactivity to human and cynomolgus TfR-1 (FIG. 1) with EC50 s of 1.5 nM and 1.6 nM for human and cynomolgus TfR-1, respectively (Table 4). No binding was observed for mouse or rat TfR-1 or for HSA, which was used as negative control.

TABLE 4

ELISA EC50 values of TXP1 for binding various species of TfR-1.

| EC50 [M] | mTfR-1 | hTfR-1 | cTfR-1 | rTfR-1 | HSA |
|---|---|---|---|---|---|
| TXP1 | NB | 1.5E-09 | 1.6E-09 | NB | NB |

NB: no binding

Binding kinetics assessed by surface plasmon resonance showed the affinity (KD) of TXP1 for human and cynomolgus TfR-1 to be approximately 1 nM and 3.1 nM, respectively (Table 5). The affinity obtained for the VNAR antibody A06 used as a comparator were approximately 3 nM and 2.6 nM for human and cynomolgus TfR-1, respectively. In Table 5, "ka" is the association rate constant, "kd" is the dissociation rate constant, and "KD" is the binding affinity.

TABLE 5

TXP1 and control A06 binding kinetics to human and cynomolgus TfR-1.

|  |  | ka [1/Ms] | kd [1/s] | KD [M] |
|---|---|---|---|---|
| TXP1 | hTfR-1 | 1.29E+05 | 1.34E-04 | 1.03E-09 |
|  | cTfR-1 | 1.16E+05 | 3.65E-04 | 3.14E-09 |

TABLE 5-continued

TXP1 and control A06 binding kinetics
to human and cynomolgus TfR-1.

|  |  | ka [1/Ms] | kd [1/s] | KD [M] |
|---|---|---|---|---|
| A06 | hTfR-1 | 1.85E+06 | 5.47E−04 | 2.95E−10 |
|  | cTfR-1 | 2.66E+05 | 7.01E−04 | 2.63E−09 |

Example 4. TXP1 Binds Human Microvascular Endothelial Cells

Flow cytometry. hCMEC/D3 cells (Weksler 2013) were seeded onto V-bottom 96-well plates at a density of $1\times10^4$ cells/well. After blocking in PBS containing 10% BSA (FACS buffer) for 20 min on ice, cells were incubated with serial dilutions of TXP1. Cells were stained with propidium iodine (PI; Biolegend) for 20 min on ice, followed by anti-hFc conjugated to Alexa488 diluted 1:300 (Jackson ImmunoResearch) for 30 min on ice. After fixation in 4% PFA for 15 min on ice, the cells were analyzed on a CytoFlex® flow cytometer (Beckman Coulter). Gating of cells stained with secondary antibody established the fluorescence threshold for the negative signal. The fluorescence intensity of approximately 1000 cells per condition was measured. Dead or dying cells were excluded from the analysis by propidium iodide staining. EC50 values were calculated using a four parametric non-linear regression model.

Figure 2:
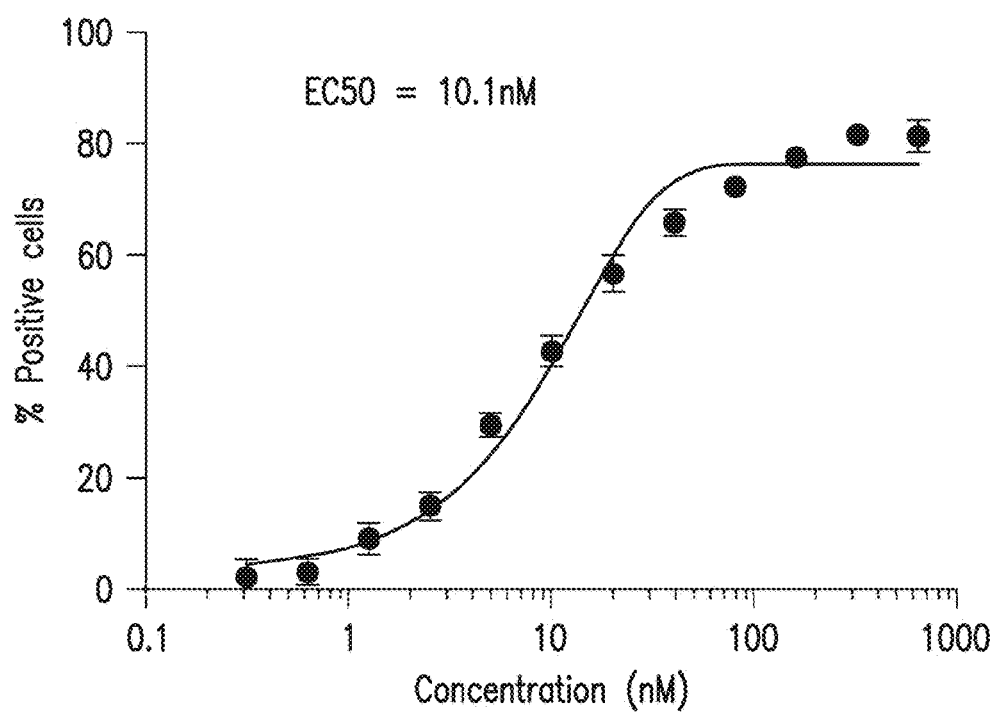
FIG. 2. Binding of TXP1 to hCMEC/D3 cells by flow cytometry. Approximately 10,000 cells were incubated with serially diluted TXP1 for 1 hour on ice. TXP1 binding was detected using anti-human IgG Alexa Fluor® 488 (hereafter "Alexa488")-conjugated secondary antibody. PI staining was used to exclude dead cells from the analysis. The cells were fixed and analyzed by flow cytometry. 1,000 cells per condition were acquired. Gating of cells stained with secondary antibody only allowed to set a fluorescence threshold for negative signal. Data presented as percentage of positive cells above the set fluorescence threshold and 4-parametric non-linear regression was used to calculate EC50 values.

Results. Binding of TXP1 to the hCMEC/D3 human brain microvascular endothelial cell line demonstrated that TXP1 binding to hCMEC/D3 cells increased with the increasing antibody concentration (FIG. 2). The calculated EC50 was 10.1 nM.

Example 5. TXP1 Binding does not Interfere with TF Binding or VNAR Internalization Cell internalization. hCMEC/D3 cells were plated onto collagen coated 96-well black plates with clear bottom (Greiner #655090) three (3) days before the assay using 10,000 cells per well in 100 μL of D3 supplemented medium that included 1 ng/mL FGF2. Serially diluted VNAR antibodies were added to the cells for 1 hour at 37° C. (5% $CO_2$) to allow binding and internalization. The cells were gently washed twice with 300 μL of PBS, then fixed in 100 μl 4% paraformaldehyde (PFA) in PBS for 15 minutes and washed again 3 times with 300 μL of PBS. Next, the cells were permeabilized with PBS-0.1% saponin for 10 minutes at RT and subsequently blocked for 30 minutes in 100 μL PBS-0.1% saponin with 5% goat serum. Detection was performed with 100 μL of secondary goat anti-human IgG Alexa488-conjugated antibody (diluted 1:200 diluted; Thermo #A11013) incubated for 1 hour in the dark. The cells were washed twice with 250 μL of PBS-0.1% TritonX-100 and incubated with 100 μL (1:10,000 dilution) of Hoechst 33342 (Thermo #H3570) for 10 min at RT. Finally, the cells were washed twice with 250 μL of PBS before images of approximately 1000 cells were captured by confocal microscopy using IN Cell Analyzer (GE Healthcare) and quantified with Cell Insight (Thermo).

Competition ELISAs. For competition studies, Maxi Sorp™ plates were coated with 100 μl of human Tf, at the concentration of 5 μg/ml overnight at 4° C. Plates were washed with phosphate-buffered saline containing 0.1% Tween20 (PBST) and blocked for 1 h with 2.5% BSA in PBST. Wells were incubated with 50 μl of hTfR-1 at 10 μg/ml for 1 h at RT and washed before adding serially diluted TXP1 and A06 VNAR antibodies for 1 h at RT. Following washing, 100 μl of 1:5,000 anti-hFc HRP-conjugated antibody (Sigma) diluted in 2.5% BSA in PBST was added and incubated for 1 h. Plates were washed and developed with SureBlue™ TMB substrate, the reaction stopped with 1% HCl and absorbance measured at 450 nm.

Cell internalization competition. The assay was performed as described above but the serially diluted VNAR antibodies were incubated with or without Tf at constant 10 μg/ml (0.143 μM) concentration. The ratio of Tf to VNAR antibodies at the highest concentration was ~10.75-fold and increased 5-fold with each subsequent VNAR antibody dilution.

Figure 3:
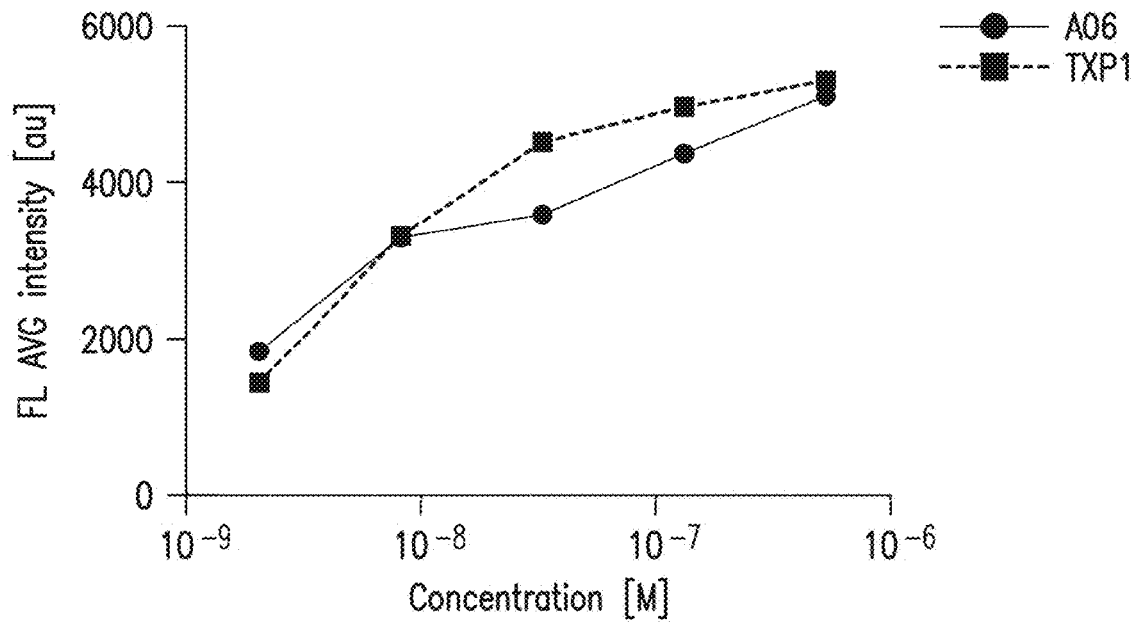
FIG. 3. hCMEC/D3 internalization of TXP1 by confocal microscopy. VNAR antibody A06, a hTfR-1 binder that competes with transferrin ("Tf"), was used for comparison (see Table 5). Adherent hCMEC/D3 cells were incubated with serially diluted VNAR antibodies (TXP1 or A06) for 1 hour. The cells were fixed and permeabilized, before staining with an anti-human IgG Alexa488-conjugated secondary antibody and nuclear counterstaining with Hoechst dye. The fluorescence intensity of approximately 1000 cells per condition was captured with an IN Cell Analyzer (GE Healthcare) and averages in arbitrary units were calculated with Cell Insight (Thermo).

Results. Internalization of TXP1 by hCMEC/D3 was assessed by confocal microscopy at antibody concentrations ranging from 2.0 nM to 0.5 μM after a 1-hr incubation at 37° C. The cells were fixed and permeabilized before staining and images were captured using an IN Cell high content image analysis system. Internalization of TXP1 was readily detected at the lowest concentration and began to plateau at approximately 50 nM (FIG. 3). A similar level of internalization was observed with the comparator antibody, VNAR antibody A06.

Figure 4:
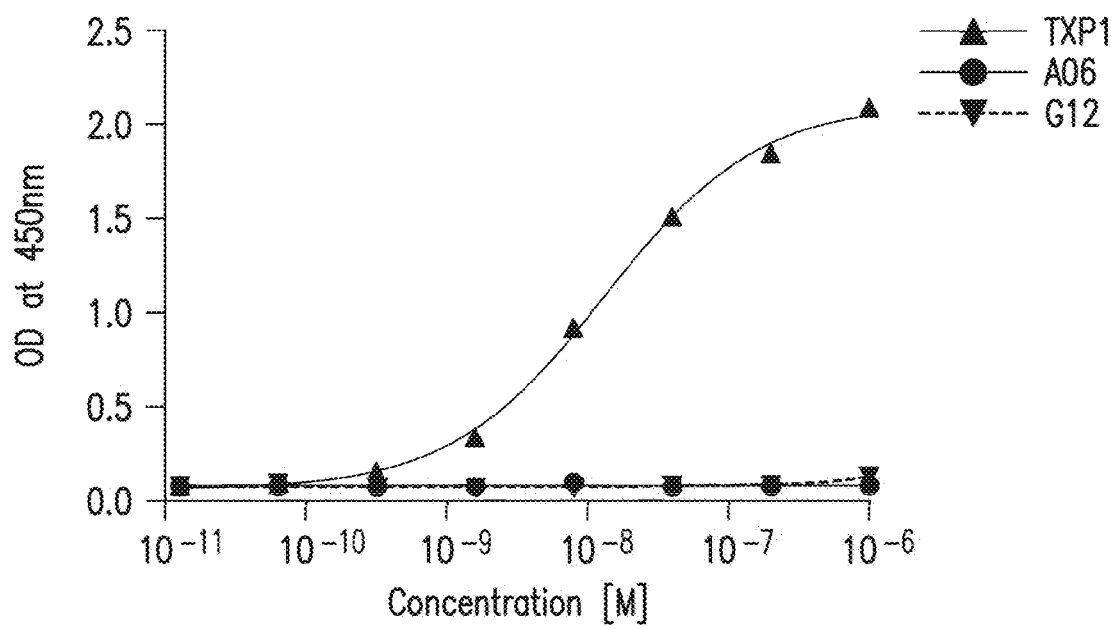
FIG. 4. Assessment of TXP1 competition with Tf by ELISA. Plates were coated with Tf and blocked before adding human TfR-1. Serially diluted VNAR antibodies were added and binding to hTfR-1 captured by Tf was measured by ELISA using anti-hFc HRP-conjugated secondary antibodies and TMB chromogen. The negative isotype control VNAR antibody G12 and the Tf-competing, hTfR-1 binder VNAR antibody A06 were used for comparison.

TXP1 competition with Tf for binding to TfR-1 was assessed by ELISA. Plates coated with Tf were used to capture hTfR-1 before incubation with serial dilutions of TXP1, A06 VNAR antibody or isotype control G12 VNAR antibody. While TXP1 and A06 VNAR antibody bind with similar nM KD in the absence of Tf (Table 5), when TfR-1 was bound to Tf, TXP1 but not the A06 VNAR antibody was still able to bind the receptor (FIG. 4). This indicated that the A06 VNAR antibody competes with Tf for TfR-1 binding while TXP1 does not. The VNAR G12 isotype control antibody did not bind TfR-1 in either the presence or absence of Tf.

Figure 5:
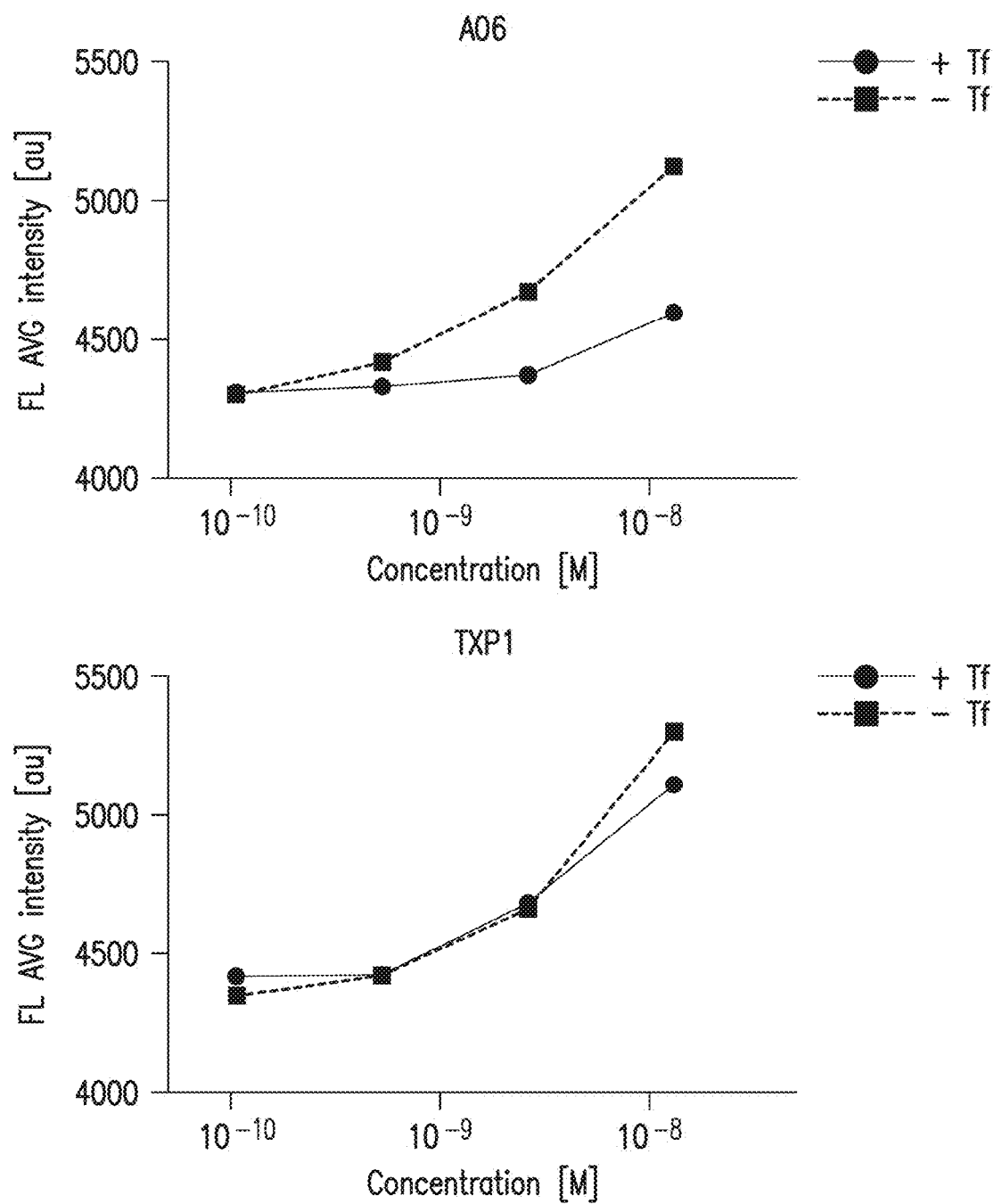
FIG. 5. Assessment of TXP1 competition with Tf by hCMEC/D3 internalization. Adherent hCMEC/D3 cells were incubated with serial dilutions of A06 VNAR antibody (top) or TXP1 (bottom) for 1 hour with or without Tf at 10 µg/ml (0.143 µM). The ratio of Tf to VNAR antibody at the highest concentration was ~10.75-fold. The cells were fixed and permeabilized before staining with an anti-human IgG Alexa488-conjugated secondary antibody and nuclear counterstaining with Hoechst dye. The fluorescence intensity of approximately 1000 cells per condition was captured with an IN Cell Analyzer (GE Healthcare) and averages in arbitrary units were calculated with Cell Insight (Thermo).
Figure 6:
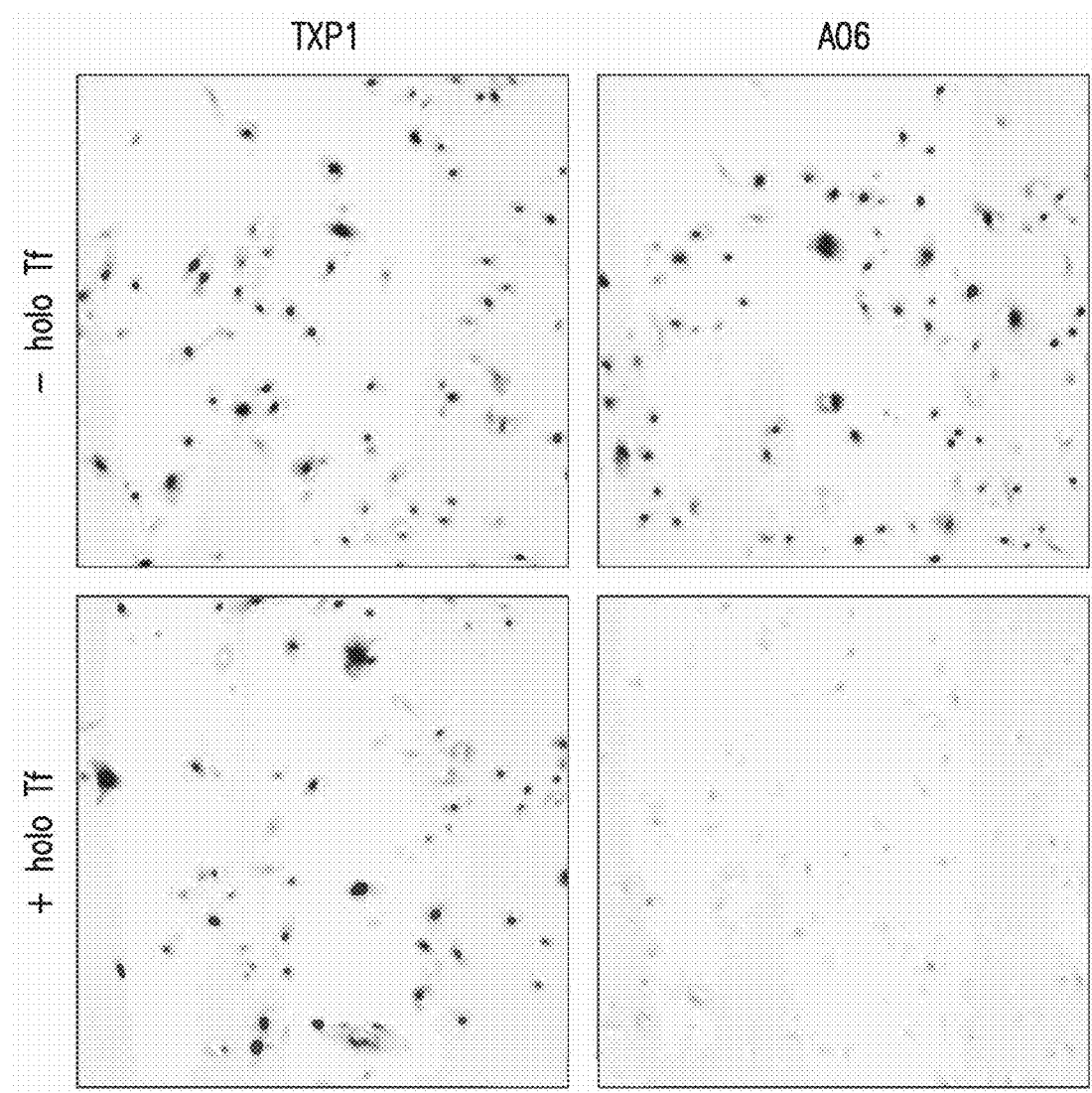
FIG. 6. Confocal microscopy images of TXP1 internalization by hCMEC/D3 cells. Adherent cells were incubated with TXP1 or A06 at 200 ng/ml (2.66 nM) with or without Tf at 10 µg/ml (0.143p M; ~50-fold molar excess) for 1 hour. The cells were fixed and permeabilized before staining with an anti-human IgG Alexa488-conjugated secondary antibody and images were captured using IN Cell Analyzer (GE Healthcare).

Competition of TXP1 with Tf for TfR-1 binding was further examined in the hCMEC/D3 cell internalization assay described above. Cells were incubated with TXP1 over a concentration range of 0.1-13.3 nM in the presence of a constant concentration of Tf (0.143 μM). The minimum molar excess of Tf at the highest VNAR concentration was 10.75-fold. The results showed that TXP1 internalized equally in the presence or absence of Tf, whereas Tf reduced the internalization of the A06 VNAR control antibody (FIG. 5). Confocal images of hCMEC/D3 cells were captured after exposure to a VNAR antibody concentration of 2.66 nM in the presence or absence of a 50-fold molar excess of Tf (0.143 μM). The images showed that Tf did not block TXP1 internalization whereas the A06 control VNAR antibody internalization was drastically reduced (FIG. 6). Thus, TXP1 did not compete with Tf in either a biochemical or cell-based assay.

Example 6. TXP1 Staining of Macaque Brain

Immunohistochemical staining. Paraffin embedded serial coronal brain sections (6 μm) from cynomolgus macaques were dewaxed in xylene and ethanol, and endogenous peroxidases quenched in 3% $H_2O_2$. Antigen retrieval was performed by boiling sections in 20 mM Tris-EDTA, pH 9.0 for 10 minutes. After blocking in 0.05 M Tris-buffered saline with 3% porcine serum albumin (TBS, pH 7.6) sections were incubated 4° C. overnight with primary antibody (TXP1, G12 at 100 μg/ml; Sigma rabbit polyclonal anti-TFRC #HPA02859 1:200). After washing in 0.025% Tween- 20 in TBS (TBST) sections were incubated with biotinylated secondary antibodies (goat anti-human IgG, monkey cross-adsorbed #A80-319, Bethyl Laboratories; goat anti-rabbit IgG #10179442, Invitrogen) at 1:500 for 1 hour at RT. Sections were washed 3× 5 min in TBS/TBST prior to incubation with avidin-biotinylated horseradish peroxidase conjugate (VectaStain ABC-HRP Kit, PK4000, Vector Labs) for 1 hour at RT. Sections were washed in TBS prior to addition of chromogenic diaminobenzidine-HRP (DAB-H; Stable DAB #10452862, Invitrogen) complex for 4 minutes. The reaction was quenched in $H_2O$ and the slides were dried, and coverslips applied using aqueous mounting media (Abcam ab64230). Brightfield images were acquired to set parameters at 10× or 20× magnification on an Olympus BX51 upright microscope using a micropublisher 6 camera and Oculus acquisition software (Teledyne Photometrics, UK).

Figure 7:
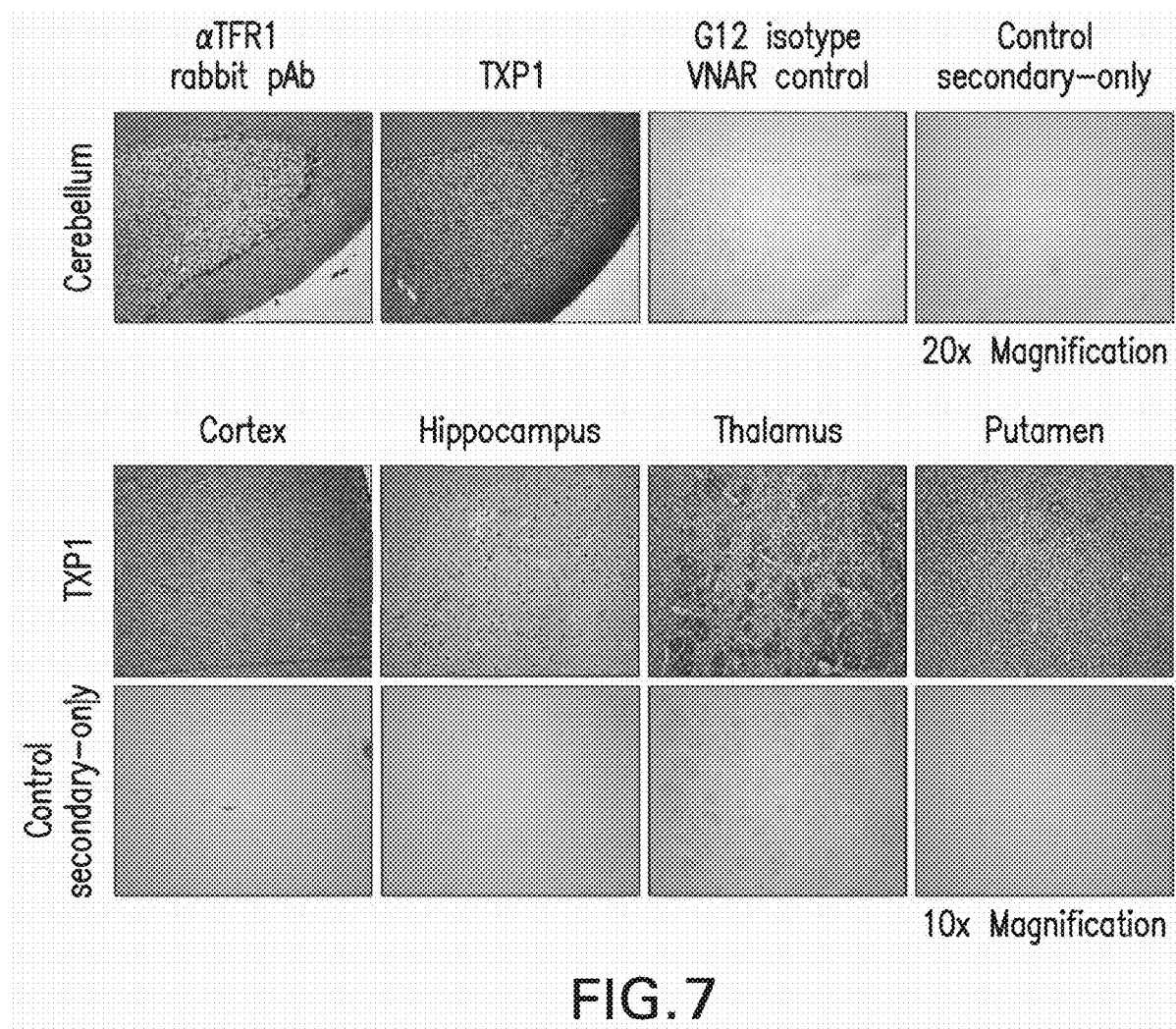
FIG. 7. Ex-vivo staining of cynomolgus brain sections with TXP1. Paraffin embedded sections were heated in 20 mM Tris-EDTA, pH 9.0 prior to incubation with primary antibodies at 100 mg/ml overnight at 4° C. Binding was detected with an HRP-conjugated goat polyclonal antibody against human IgG cross-adsorbed against monkey IgG (Bethyl Laboratories). Staining of TXP1 in the cerebellum (top row) is shown in comparison to a rabbit polyclonal antibody against TfR-1 (Sigma), the VNAR antibody G12 isotype control and the secondary antibody alone control. TXP1 staining in additional brain regions (middle row) is shown compared to the secondary antibody only control (bottom row).

Results. Ex vivo immunohistochemical staining of brain sections from cynomolgus macaques with TXP1 shows strong immunoreactivity and localization predominantly in the cell bodies of cerebellum lobule, Purkinje cells and neurons in grey matter regions of the mid-brain (FIG. 7). The staining intensity and regional distribution for TXP1 was comparable to commercially available polyclonal rabbit anti-TfR-antibodies. Specificity was confirmed by parallel immunohistochemical staining with the G12 isotype VNAR control and the secondary antibody alone, since both were unreactive.

Example 7. Brain Uptake and Distribution in Macaque Brain

Tissue ELISA. MaxiSorp™ plates were coated with 100 µl of mouse anti-human IgG-CH2 domain (Thermo #MA5-16929) diluted 1:1000 in PBS overnight at 4° C. Plates were washed and incubated with blocking buffer for 1 h at RT. Tissue samples from brain regions were homogenized in 3:1 (v/w) PBS containing 1% Triton X-100 supplemented with protease inhibitors (Complete™, Sigma) using the TissueeRuptor® homogenizer (Qiagen) at medium speed for 10 sec and then incubated for 30 min on ice. Lysates were spun down at 17,000×g for 20 min; the supernatant was collected and blocked in 2.5% milk in PBST overnight at 4° C. Blocked brain lysates (100 µl) were added to the blocked plates and incubated for 1 h at RT. Plates were washed with PBST and incubated with a goat anti-human Fc-peroxidase antibody diluted 1:5000 (Sigma) in blocking buffer for 1 hour. Plates were washed and developed with SureBlue™ TMB substrate, the reaction stopped with 1% HCl and absorbance measured at 450 nm. The VNAR-Fc concentration was determined from standard curves prepared individually for each fusion protein.

Brain Uptake. Brain penetration was evaluated in non-human primates using TXP1 and VNAR G12 antibodies prepared with >96% purity and endotoxin levels below 2 EU/mg. Two cynomolgus macaques per group were dosed with 1.35 mg/kg, IV. Blood and CSF was collected 20 hours post injection and brains were extracted following cardiac prefusion.

Figure 8:
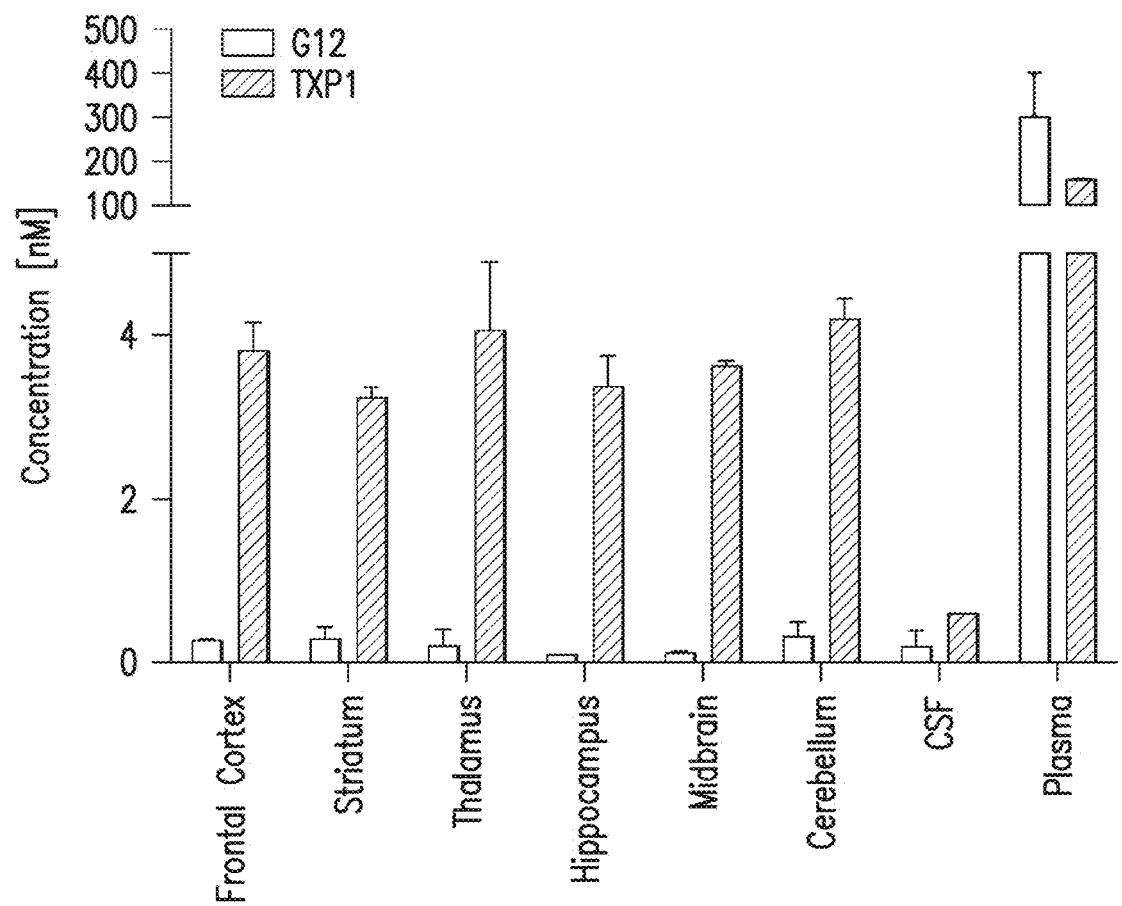
FIG. 8. Brain penetration by TXP1 in cynomolgus macaques. Animals were injected with 1.35 mg/kg IV of TXP1 or G12 negative control. At 20 hours post injection, the animals were sacrificed, and blood and CSF were collected prior to cardiac perfusion. Specific regions were dissected and homogenized in 1% Triton X-100. Blocked samples were added to ELISA plates coated with anti-hFc specific antibodies and TXP1 was detected with polyclonal anti-hFc-HRP and TMB chromogen. Absorbance was measured at 450 nm and the absolute concentration was calculated by 4-parametric non-linear regression from the standard curves prepared individually for each sample. The mean±SD (N=2) are shown.
Figure 9:
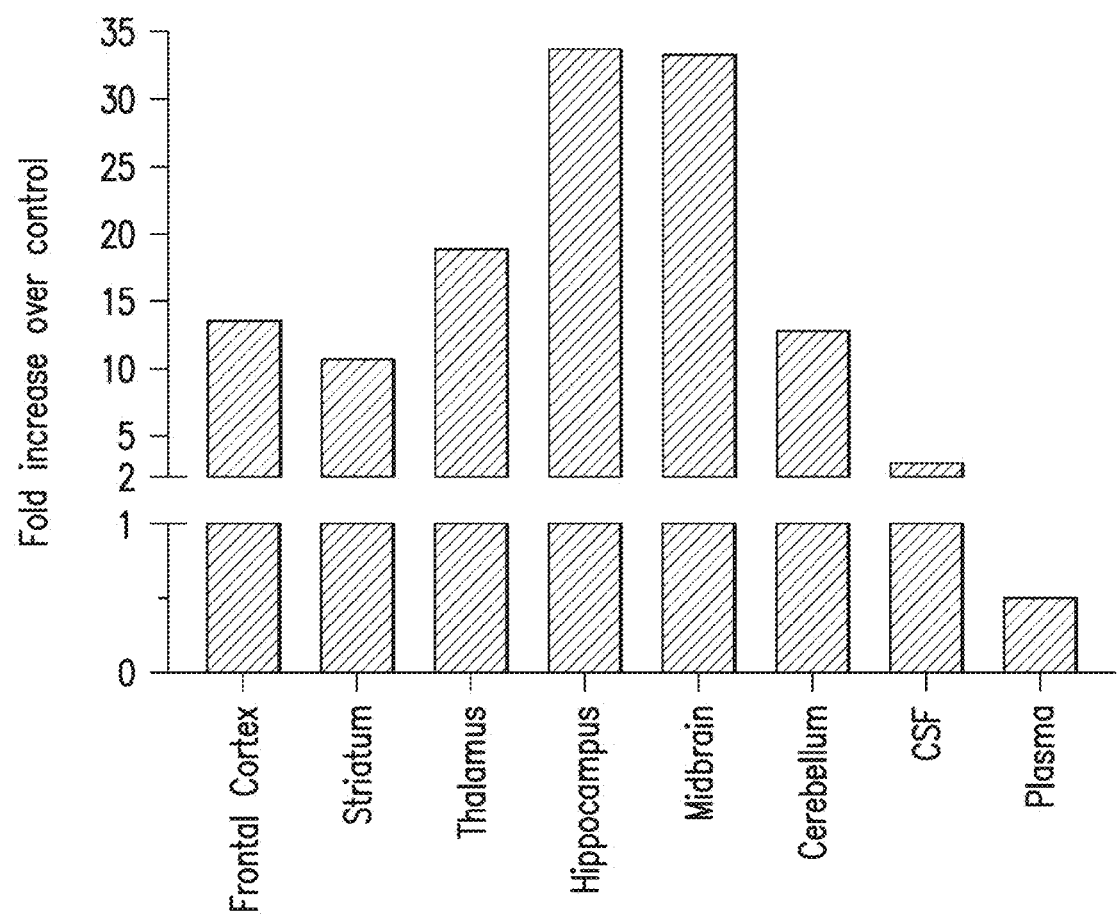
FIG. 9. Regional brain concentrations of TXP1 expressed as fold difference relative to the negative control VNAR antibody G12. The absolute concentrations measured in brain tissue, CSF and plasma are from FIG. 8.
Figure 10:
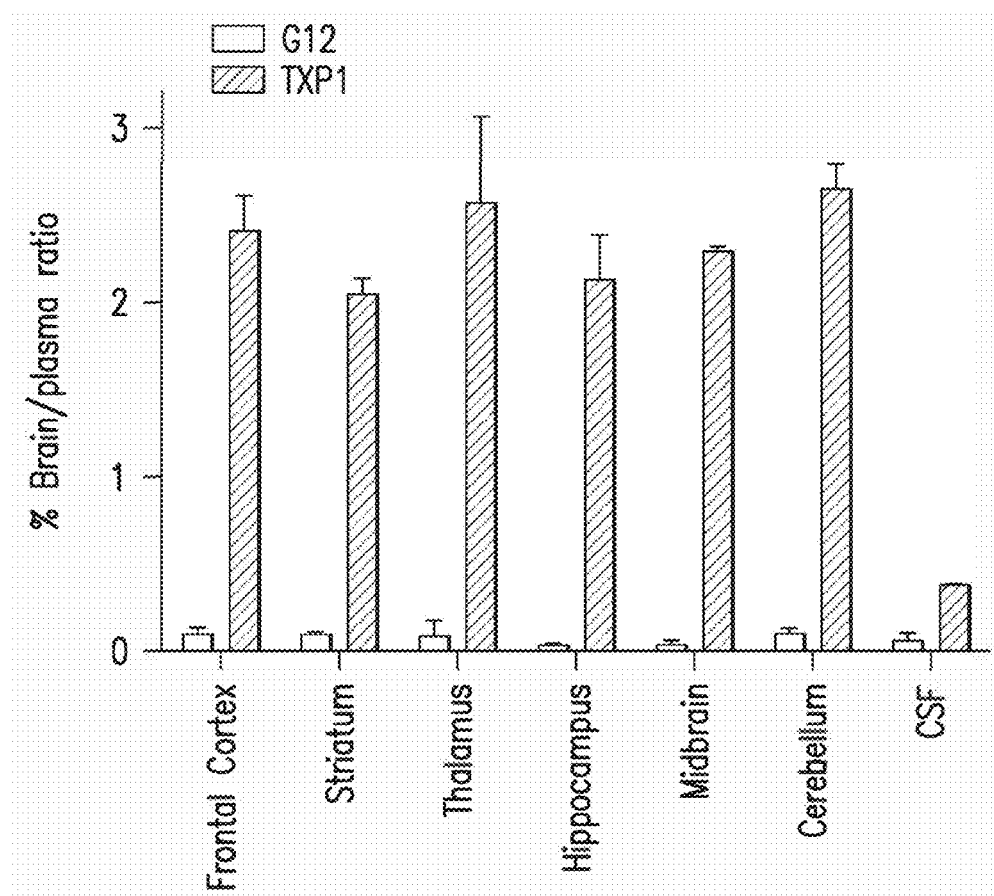
FIG. 10. Brain and CSF to plasma ratios for TXP1 and negative control G12. The absolute concentrations measured in brain tissues and CSF were divide by plasma concentrations (from FIG. 8) and expressed as percentages.

Results. The absolute brain concentrations in specific regions (frontal cortex, striatum, thalamus, hippocampus, midbrain and cerebellum) as measured by ELISA ranged from 3.2-4.2 nM for TXP1 and 0.1-0.3 nM for G12 (FIG. 8). Levels of TXP1 in the regional brain samples were significantly higher (approximately 6-fold) than that in the CSF (0.6 nM), whereas G12 showed similar concentration in brain samples and CSF (0.2 nM). Plasma levels 20 h post injection were approximately 160 nM and 300 nM for TXP1 and G12, respectively. The difference between TXP1 and the G12 negative control VNAR antibody was highest in the hippocampus and midbrain, reaching ~35-fold (FIG. 9). TXP1 levels in frontal cortex, striatum, thalamus, and cerebellum were 10- to 20-fold higher than the negative control while only 3-fold higher in the CSF. Plasma levels for TXP1 in comparison to G12 were reduced possibly due to the increased brain penetration of TXP1. Brain/plasma ratios for TXP1 in various brain regions ranged from 2.0-2.6% and the CSF to plasma ratio was 0.4% (FIG. 10). The brain/plasma ratio of the G12 negative control was significantly lower, ranging from 0.03-0.1% in various brain regions and the CSF to plasma ratio was 0.06%.

In summary, the above Examples show that TXP1 reacts with human and non-human primate (NHP) TfR-1 in vitro and penetrates the NHP brain in vivo. TXP1 specifically bound to recombinant human and cynomolgus TfR-1 with a high affinity (1 nM and 3 nM KD, respectively) and without interference with the natural ligand Tf. Likewise, TXP1 bound to and was internalized by hCMEC/D3 cells, a model of the expressing TfR-1 cell target in the human BBB, without Tf interference. When applied directly to sections from NHP brain tissue, TXP1 reacted with brain regions in a pattern that mimics the expression of endogenous TfR-1 with predominant staining in neuronal cell bodies that strongly express the receptor. After IV administration of TXP1 to NHPs at a low therapeutic dose (1.35 mg/kg), absolute brain concentrations of approximately 4 nM were measured in all sampled brain regions with brain/plasma ratios of at least 2%. Conversely, low levels were found in CSF (0.6 nM) and the CSF/plasma ratio was proportionally lower (0.4%). These results indicate that the presence of TXP1 in the brain is mediated by transport across the capillary endothelium of the BBB rather than across the choroid plexus into CSF. The results with TXP1 in NHP are highly consistent with the level of brain penetration observed in mice injected with a different high-affinity VNAR antibody to TfR-1 (Stocki 2020).

Example 8. TXP1 Brain Distribution

Immunohistochemistry (IHC). To assess brain penetration of TXP1 in vivo, one hemisphere from each animal injected with either TXP1 or the negative control G12 (1.35 mg/kg IV) was post-fixed in formalin after cardiac perfusion with PBS. Brains were washed in 0.01M potassium phosphate-buffered saline (PPBS), immersed in 30% sucrose and frozen sections (40 µm) were cut on a cryostat (Leica CM3050 S). Free-floating brain sections were incubated in blocking buffer (3% porcine serum diluted in 0.01 M PPBS with 0.3% Triton X-100) for 60 min at RT and then incubated overnight at 4° C. with biotinylated goat anti-human IgG antibody (Vector, BA 3000) diluted 1:200 in blocking buffer. After 24 h, the sections were washed twice in washing buffer (blocking buffer diluted 1:50 in PPBS) and once in PPBS. Antibodies were visualized by addition of Avidin-Biotin Complex-system (ABC-HRP kit, Vector) for 30 min at room temperature followed by 3,3'-diaminobenzidine tetrahydrochloride for 10 min.

Figure 11:
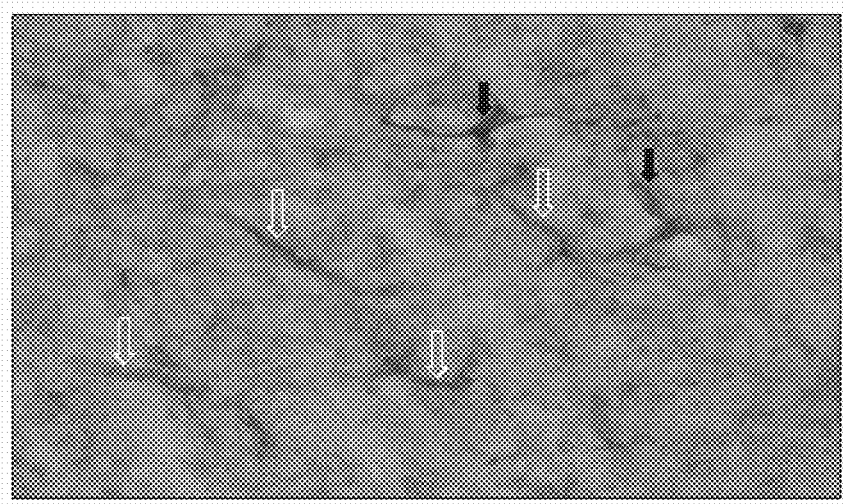
FIG. 11. Immunohistochemical localization of TXP1 in cynomolgus brain after intravenous administration. Transcardial perfusion with PBS was performed 20 hrs after injection of either TXP1 or negative control G12 at 1.35 mg/kg. One hemisphere from each animal was post-fixed in formalin, immersed in sucrose, and 40 µm frozen sections were cut on a cryostat. Free-floating sections were incubated with a biotinylated goat anti-human IgG antibody and staining detected with an ABC-HRP system. Diffuse TXP1 staining throughout the brain parenchyma with TXP1 localized within neurons (black arrows) and capillary endothelial cells (white arrows), with a neuron shown at higher magnification (inset). Neither the G12 control nor the staining controls showed any selective staining of cellular or vascular elements.

Results. TXP1 immunoreactivity was clearly evident within the brain after IV dosing at 1.35 mg/kg. As illustrated in sections from the cerebral cortex (FIG. 11), TXP1 was found not only in brain capillaries, but also diffusely throughout the brain parenchyma and within neurons. The neuronal staining pattern of TXP1 in the cortex after IV administration closely mimicked that seen after direct antibody application to paraffin sections from untreated animals (FIG. 7). By contrast, the VNAR-G12-hFc control did not show any selective staining of cellular or vascular elements. In summary, the IHC results confirm that a high-affinity, bivalent VNAR antibody to TfR-1 crosses the BBB and is not retained within the brain capillaries as commonly observed with monoclonal antibodies to TfR-1.

Figure 12:
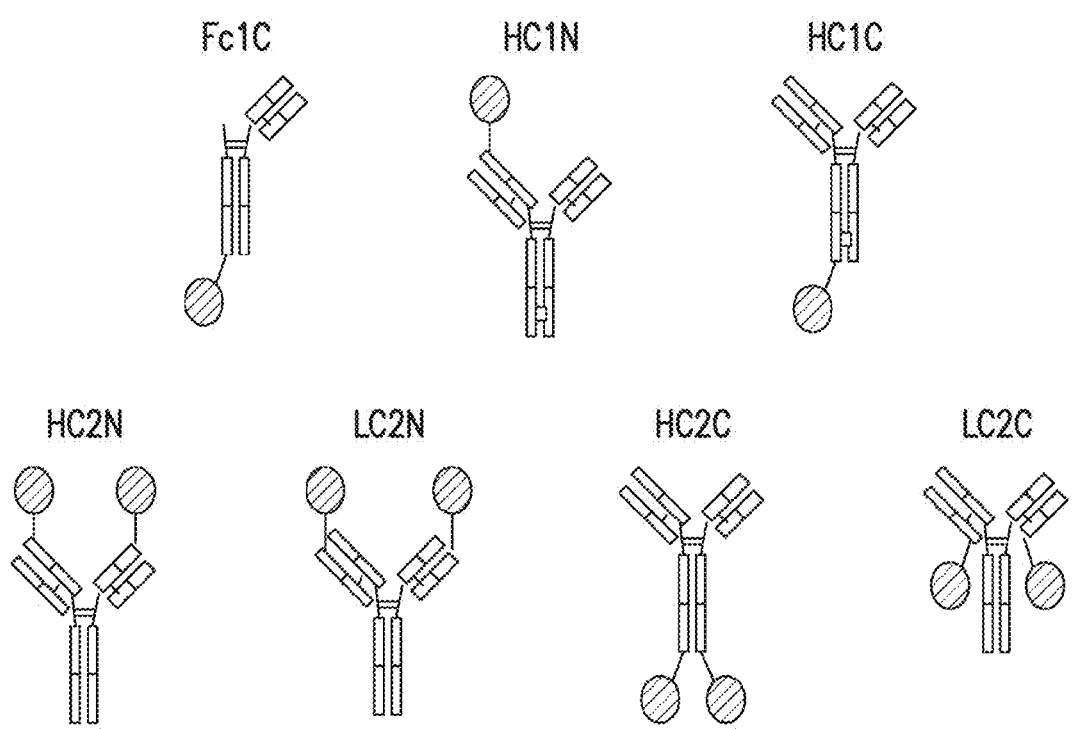
FIG. 12. Examples of VNAR-Antibody Fusion Proteins. Antibodies with a monovalent VNAR (top row) or bivalent VNARs (bottom row) genetically fused to a monoclonal antibody via glycine linkers.

Example 9. TXP1-Mediated In Vivo Transport of a Therapeutic Antibody Across the Blood Brain Barrier Brain shuttling efficacy of TXP1 can also be tested by genetically fusing its VNAR domain (VNAR-txp1) to different therapeutic antibodies. Rituximab (RIT), bapineuzumab (BAPI) and durvalumab (DUR) can be used as model antibodies in different mono- and bi-valent formats (FIG. 12). Injection into macaques is done as in Example 7 or into mice as described in the paragraph below.

Balb/c mice (6-8 weeks) are injected intravenously with from 12.5 nmol/kg (0.9375 mg/kg) of protein to 25 nmol/kg and a blood sample is taken after 18 h. The animals are then perfused, and the brains are dissected and stored frozen. The whole brains are homogenized in 1% Triton X-100 and used for ELISA with anti-Fc capture and detection antibody. Standard curves can be prepared individually for each of the molecules to assure accuracy of the calculated concentrations. R3D11 and 1A can serve as negative VNAR-Fc controls that bind at nM concentration to TfR-1 but lack a blood brain penetration property.

Example 10. Plasma Pharmacokinetics (PK) of TXP1

To assess the plasma PK profile of TXP1, cynomolgus macaques were injected i.v. with TXP1 or G12 isotype control at 1.35 mg/kg and plasma samples were collected over a 28-day period, ranging from 1 hr to 28 days. Plasma concentrations were measured by ELISA and various PK parameters were calculated using PKSolver [Zhang 2010]. The AUC values for G12 and TXP1 were 30.4 and 8.6 µMh, respectively. The relative reduction in plasma concentration for TXP1 (approximately 3.5-fold) seen during the distribution phase can be attributed to binding the large pool of TfR1 receptors at the BBB and transport into the brain. This is consistent with the up to 35-fold increase of TXP1 concentration in the brain over G12 at the 20-hr timepoint (FIGS. 8 and 9).

Figure 13:
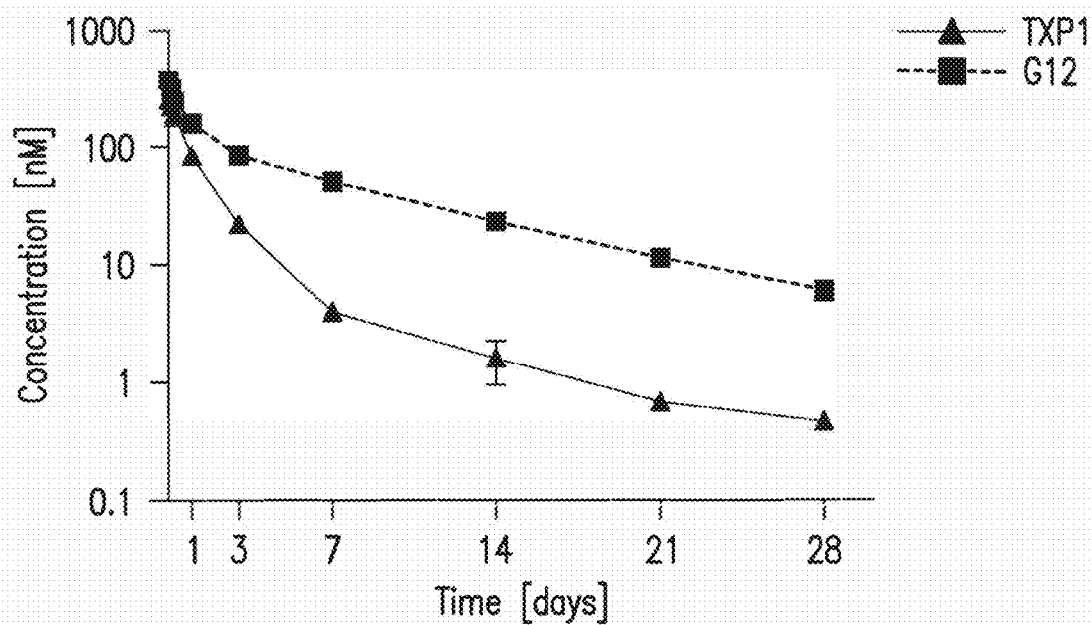
FIG. 13. Single dose plasma PK profile of TXP1 in cynomolgus macaques. Animals were injected with 1.35 mg/kg IV of or G12 isotype control and 9 blood samples were collected in total, ranging from 1 hr to 28 days post injection. Plasma antibodies concentrations were measured by ELISA and PK parameters were calculated with PKSolver. Data presented as mean, ±SD (n=2). AUC—area under the curve, MRT—median residence time, Cmax—maximal concentration, t½—half-life in the elimination phase.

Results. The plasma half-life calculated from the elimination phase for G12 and TXP1 was 176 and 161 hr, respectively (FIG. 13 and Table 6). Since the elimination half-life of TXP1 was very similar to the control, there is no indication of accelerated target-mediated metabolism. In contrast, the reported plasma half-life for various high-affinity monoclonal antibodies to TfR1 range from 2 to 6 hr in rat, mouse, and monkey (Pardridge 1991; Boado 2009; Pardride 2018). These antibodies also bind to TfR1 expressed at high levels in the liver, leading to enhanced clearance through the Fc domain-mediate metabolic pathway for monoclonal antibodies (Ovacik 2018). The comparable high-affinity VNAR TXB2 antibody in mice is brain selective and does not accumulate is the liver (Stocki 2021; Sehlin 2020). Like TXP1, TXB2 also has a normal elimination rate and long half-life (approximately 6.5 days), which represents a major advantage of VNAR-based BBB shuttles.

TABLE 6

| Parameter | Unit | TXP1 | G12 |
|---|---|---|---|
| t½ | hr | 161 | 176 |
| Cmax | nM | 259 | 377 |
| Clast_obs/Cmax | | 0.0018 | 0.0166 |
| AUC 0-inf_obs | nM*h | 8563 | 30440 |
| MRT 0-inf_obs | hr | 65.8 | 192.6 |

Data presented as mean, ±SD (n = 2).
AUC—area under the curve, MRT—median residence time, Cmax—maximal concentration, t½—half-life in the elimination phase.

Example 11. TXP1 does not Alter TfR-1 Levels in the Brain or Lead to Reticulocyte Clearance Endogenous levels of TfR-1 were measured in cynomolgus macaques after a 20-hr exposure to TXP1 dosed at 1.35 mg/kg. The extracts from various brain regions were analysed by western blotting for relative quantification of TfR-1 against actin. For western blotting, whole brain tissue samples were homogenized in 3:1 (v/w) of PBS containing 1% Triton X-100 supplemented with protease inhibitors (COmplete™, Sigma) using the TissueRuptor® homogenizer (Qiagen) at medium speed for 10 seconds and incubated for 30 minutes on ice. Lysates were centrifuged (20 min at 17 000×g) and the protein concentration of the supernatant was determined (BCA assay, Thermo Fisher). Samples (30 µg/well) were resolved by SDS-PAGE under reducing conditions and transferred onto membranes (PVDF, Thermo Fisher). After blocking with 2% BSA for 30 min, membranes were incubated with mouse anti-TfR-1 clone H68.4 (Thermo Fisher) and rabbit anti-actin antibodies (Abcam). Binding was detected with an anti-mouse Cy-3 and anti-rabbit Cy-5 antibodies (Cytiva). Blots were scanned using a Typhoon™ imager (Cytiva) and the signal intensity was quantified using Image Studio Lite (LI-COR Biosciences).

As with the high-affinity TXB2 VNAR antibody in mice (Stocki 2021), no difference was observed in endogenous Tf-1 levels in macaques injected with TXP1 relative to the G12 isotype control.

Reticulocytes express high levels of TfR-1 and immune-mediated clearance with a subsequent reduction in circulating red blood cells has been observed after treatment with high-affinity TfR1 antibodies with wild type Fc carrying full effector function [Pardridge 2018; Couch 2013). TXP1 and G12 contain the LALA-PG mutations and should be devoid of effector function.

Blood samples were obtained after a 24-hr exposure to TXP1 dosed at 1.35 mg/kg. The samples were mixed with 20 µg/ml specific anti-hFc Alexa Fluor®-647 conjugated antibodies (Thermo Fisher) for 30 minutes at RT. Antibody binding to the reticulocyte population was determined by flow cytometry using CytoFlex® cell sorter (Beckman Coulter). Cells were subsequently washed, diluted 1:5 with PBS and 10 µl aliquots were added to 1 ml of BD Retic-Count reagent (BD Biosciences). After a 60-minute incubation in the dark at RT, the samples were analysed by flow cytometry using CytoFlex® cell sorter (Beckman Coulter).)

As expected, TXP1 bound to reticulocytes, but did not reduce the reticulocyte circulating population in cynomolgus macaques after a 24-hr exposure to TXP1

Example 12. TXP1 Binds Human Brain Sections

Figure 14:
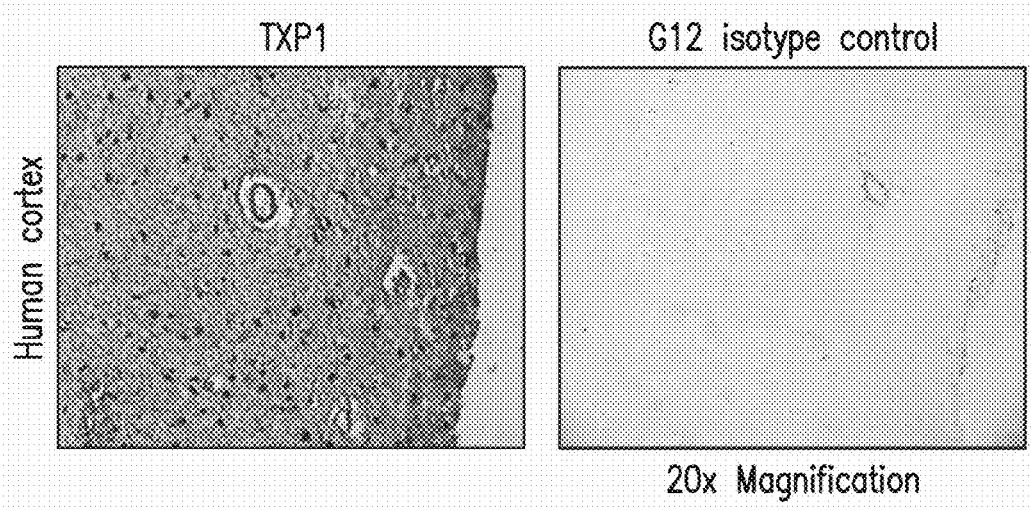
FIG. 14. Ex-vivo staining of human brain cortex with TXP1. Paraffin embedded sections were heated in 20 mM Tris-EDTA, pH 9.0 prior to incubation with primary antibodies at 100 µg/ml overnight at 4° C. Binding was detected with an HRP-conjugated goat polyclonal antibody against human IgG cross-adsorbed against monkey IgG (Bethyl Laboratories). Staining of TXP1 in the cortex (left panel) is shown in comparison to the G12 isotype control (right panel).

Strong immunoreactivity was observed when TXP1 was used for ex-vivo IHC staining of the human brain cortex, whereas there was no signal for the G12 control generally as described in Example 8 (FIG. 14). Ex-vivo IHC staining with TXP1 on brain sections from cynomolgus macaque also produced a very strong immunoreaction in cortex in addition to all other brain regions examined (cf., FIG. 7).

Example 13. Deimmunized VNAR Scaffolds

Figure 15:
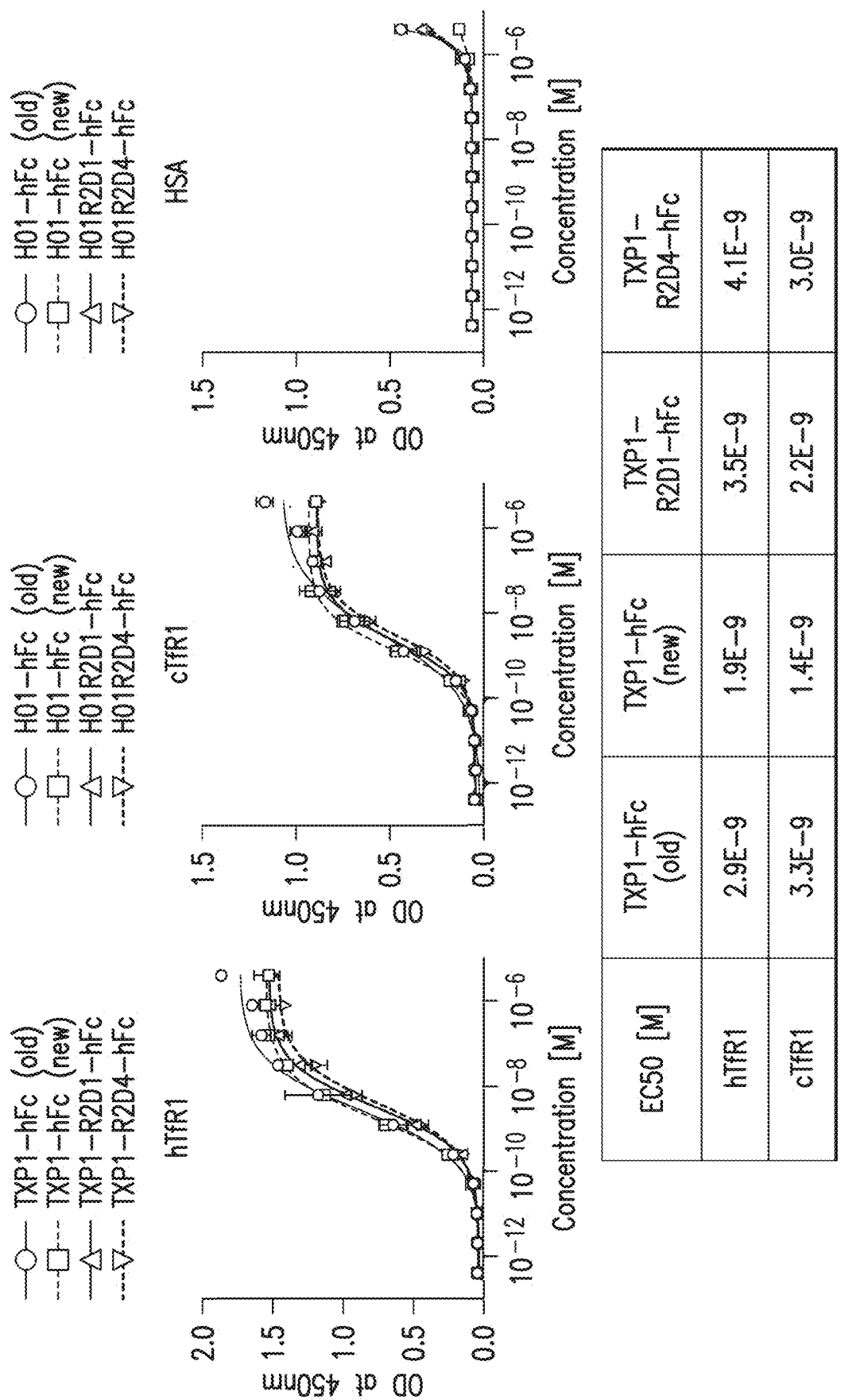
FIG. 15. Binding activity of TXP1 and deimmunized variants assessed by ELISA. Plates were coated with either human or cynomolgus or rat TfR-1. HSA was used as a negative control. Serial dilutions of TXP1 (a VNAR antibody) or the variants as Fc fusions were added to the plate and binding was measured by end-point ELISA upon incubation with secondary anti-hFc HRP-conjugated antibodies and visualization with TMB. Absorbance was measured at 450 nm and 4-parametric non-linear regression was used to calculate EC50 values (see bottom panel).

The VNAR scaffold from VNAR-txp1 was analysed in silico to identify human T-cell epitopes (Reynisson 2020) and possible amino acid substitutions for those positions in such epitopes were determined from a next generation sequence (NGS) databank from shark immune libraries. VNAR-txp1 variants with the selected non-immunogenic substitutions (Table 3) were prepared and analysed for binding activity and stability. The deimmunized TXP1 variants TXP1D1 (aka R2D1) and TXP1D4 (aka R2D4) show no strong HQ HLA class II binders and no loss of TfR binding activity by ELISA (FIG. 15).

Example 14. Further Analysis of Deimmunized VNAR Scaffolds

Results. The two fully deimmunized variants, TXP1D1 and TXP1D4, that differed only in modifications in region 2, had similar binding and expression levels to the parental TXP1. These variants were produced at the 100 ml scale for further evaluation. While expression and purification parameters for TXP1D1 and TXP1D4 were like the parental TXP1, but both variants showed higher expression yields and lower purity as determined by analytical SEC (Table 7). However, after a two-step purification with the addition of preparative SEC, the final purification yields of TXP1 and TXP1D4 were similar, whereas the yield of TXP1D4 was approximately 60% higher than the parental TXP1. Melting temperature was assessed by thermal shift and showed similar results for TXP1, TXP1D1 and TXP1D4, approximately 61° C. (Table 7), indicating that the introduced mutations did not affect antibody stability under heat stress.

Binding of TXP1D1 and TXP1D4 to hTfR-1 and cTfR-1 by ELISA showed very similar single digit nM EC50 values to TXP1 (Table 7). The binding kinetics (affinity, on- and off-rates) as measured by SPR were also very similar between TXP1D1, TXP1D4 and TXP1, with affinities of approximately 3-5 nM for hTfR-1 and 2 nM cTfR-1. Functional activity of the fully deimmunised variants was assessed using the human endothelial cell line hCMEC/D3 and the human neuronal cell line SY-SH5Y. Binding to hCMEC/D3 cells was assessed by incubation with serial antibody dilutions for 1 h on ice to avoid internalisation. The cells were fixed and binding to cell surface TfR1 was measured by flow cytometry. Cell binding EC50 values for TXP1, TXP1D1 and TXP1D4 of approximately 2.2 nM, 1.6 nM and 2.1 nM, respectively were very similar (Table 7). Internalisation via cell-surface hTfR1 was assessed using the hCMEC/D3 and SY-SH5Y cell lines by incubation with the antibodies for 1 hour at 37° C. Fluorescent microscopy showed a similar level of internalisation between TXP1 and the deimmunised variants in both cell lines

TABLE 7

Comparative properties of TXP1, TXP1D1 and TXP1D4

| Parameter | TXP1 | TXP1D1 | TXP1D4 |
|---|---|---|---|
| Expression yield [mg/l] | 49 | 78 | 65 |
| Expression quality (monomer peak) [%] | 92.3 | 82.4 | 65.7 |

TABLE 7-continued

Comparative properties of TXP1, TXP1D1 and TXP1D4

| Parameter | TXP1 | TXP1D1 | TXP1D4 |
|---|---|---|---|
| Purification yields (>97% purity) [mg/l] | 24 | 38.5 | 25 |
| Tm by thermal shift assay [° C.] | 61.14 | 60.92 | 60.82 |
| hTfR1 binding EC50 by ELISA [M] | 1.9E−09 | 3.5E−09 | 4.1E−09 |
| cTfR1 binding EC50 by ELISA [M] | 1.4E−09 | 2.2E−09 | 3.0E−09 |
| hTfR1 affinity KD by SPR [M] | 5.1E−09 | 4.6E−09 | 3.0E−09 |
| hTfR1 on-rate by SPR [1/Ms] | 5.4E+04 | 6.7E+04 | 8.7E+04 |
| hTfR1 off-rate by SPR [1/s] | 2.7E−04 | 3.1E−04 | 2.6E−04 |
| cTfR1 affinity KD by SPR [M] | 1.8E−09 | 2.2E−09 | 1.7E−09 |
| cTfR1 on-rate by SPR [1/Ms] | 5.3E+04 | 7.3E+04 | 8.7E+04 |
| cTfR1 off-rate by SPR [1/s] | 9.6E−05 | 1.6E−04 | 1.4E−04 |
| hCMEC/D3 cell binding EC50 [M] | 2.2E−09 | 1.6E−09 | 2.1E−09 |

REFERENCES

Boado et al (2009) "Engineering and Expression of a Chimeric Transferrin Receptor Monoclonal Antibody for Blood-Brain Barrier Delivery in the Mouse," Biotechnol. Bioeng. 102:1251-8.

Couch et al. (2013) "Addressing safety liabilities of TfR bispecific antibodies that cross the blood-brain barrier." Sci. Transl. Med. 5(183): 183ra57, 1-12.

Daniels et al. (2006) "The transferrin receptor part I: Biology and targeting with cytotoxic antibodies for the treatment of cancer." Clin. Immunol. 121:144-58.

Demogines et al. (2013). "Dual host virus arms races shape an essential housekeeping protein." PLoS Biol. 11(5): e1001571.

Forejtnikovà et al. (2010) "Transferrin receptor 2 is a component of the erythropoietin receptor complex and is required for efficient erythropoiesis," Blood 116:5357-67.

Gerhardt et al. (1991) "The cDNA sequence and primary structure of the chicken transferrin receptor." Gene 102: 249-54.

Kariolis et al. (2020) "Brain delivery of therapeutic proteins using an Fc fragment blood-brain barrier transport vehicle in mice and monkeys." Sci. Transl. Med. 12:eaay1359.

Konning et al. (2017) "Camelid and shark single antibodies: structural features and therapeutic potential." Curr. Opin. Struct. Biol. 45:10-16.

Lo et al. (2017) "Effector-attenuating Substitutions That Maintain Antibody Stability and Reduce Toxicity in Mice." J. Biol. Chem. 292: 3900-3908.

Niewoehner et al. (2014) "Increased Brain Penetration and Potency of a Therapeutic Antibody Using a Monovalent Molecular Shuttle," Neuron 81:49-60.

Ovacik et al. (2018) "Tutorial on Monoclonal Antibody Pharmacokinetics and Its Considerations in Early Development." Clin. Transl. Sci. 11(6): p. 540-552.

Pardridge et al. (1991) "Selective transport of an anti-transferrin receptor antibody through the blood-brain barrier in vivo." J Pharmacol Exp Ther. 259(1): p. 66-70.

Pardridge et al. (2018) "Blood-Brain Barrier Transport, Plasma Pharmacokinetics, and Neuropathology Following Chronic Treatment of the Rhesus Monkey with a Brain Penetrating Humanized Monoclonal Antibody Against the Human Transferrin Receptor." Mol. Pharm. 15: 5207-5216.

Reynisson et al. (2020) "Improved Prediction of MHC II Antigen Presentation through Integration and Motif Deconvolution of Mass Spectrometry MHC Eluted Ligand Data," J Proteome Res. 19:2304-2315.

Sehlin et al. (20200 "Brain delivery of biologics using a cross-species reactive transferrin receptor 1 VNAR shuttle.' FASEB J. 34(10): 13272-13283.

Silvestri et al. (2014) "The extrahepatic role of TFR2 in iron homeostasis," Front. Pharmacol. 5:93, 6 pages.

Stocki et al. (2020) "Blood-brain barrier transport using a high-affinity, brain-selective VNAR (Variable Domain of New Antigen Receptor) antibody targeting transferrin receptor 1." bioRxiv preprint, posted Jul. 20, 2020.

Stocki et al. (2021) "Blood-brain barrier transport using a high affinity, brain-selective VNAR antibody targeting transferrin receptor 1." FASEB J. 35(2): p. e21172.

Weksler et al. (2013) "The hCMEC/D3 cell line as a model of the human blood brain barrier." Fluids Barriers CNS 10:16.

White et al. (1990) "Combinations of anti-transferrin receptor monoclonal antibodies inhibit human tumor cell growth in vitro and in vivo: evidence for synergistic antiproliferative effects." Cancer Res. 50:6295-301.

White et al. (1992). "Monoclonal antibodies against defined epitopes of the human transferrin receptor cytoplasmic tail." Biochim. Biophys. Acta. 11136(1):28-34.

Yu et al. (2014) "Therapeutic bispecific antibodies cross the blood-brain barrier in nonhuman primates," Sci. Transl. Med. 3:84ra44, 10 pages.

Zhang, Y., et al., (2010) "PKSolver: An add-in program for pharmacokinetic and pharmacodynamic data analysis in Microsoft Excel," Comput Methods Programs Biomed. 99(3): p. 306-14.

We claim:

1. A Type II VNAR polypeptide which comprises a VNAR domain capable of specifically binding to human TfR-1 without substantially interfering with transferrin binding to and/or transport by human TfR-1, wherein said VNAR domain is represented by the formula, from N to C terminus, FW1-CDR1-FW2-HV2-FW2'-HV4-FW3-CDR3-FW4, and wherein the CDR1 region has an amino acid sequence of DSNCALSS (SEQ ID NO. 1) and the CDR3 region has an amino acid sequence of VVGTWCMSWRDV (SEQ ID NO. 2).

2. The VNAR polypeptide of claim 1, wherein the HV2 region has an amino acid sequence of TNEENISKG (SEQ ID NO. 3).

3. The VNAR polypeptide of claim 1, wherein the HV4 region has an amino acid sequence of SGSKS (SEQ ID NO. 4).

4. The VNAR polypeptide of claim 1, wherein said VNAR domain comprises an amino acid sequence of any one of SEQ ID NOS. 5-7.

5. The VNAR polypeptide of claim 1 or 4 which further comprises at least one diagnostic or therapeutic agent to thereby form a conjugate.

6. The VNAR polypeptide of claim 5, wherein said agent is selected from the group consisting of one or more of a small molecule, a DNA, RNA, or hybrid DNA-RNA, a traceable marker such as a fluorescent or phosphorescent molecule, a radionuclide or other radioactive agent, an antibody, single-chain variable domain, immunoglobulin fragment, variant or fusion, a small molecule diagnostic or therapeutic.

7. The VNAR polypeptide of claim 6, wherein said agent is an immunoglobulin fragment.

8. The VNAR polypeptide of claim 7, wherein said immunoglobulin fragment is an Fc domain.

9. A pharmaceutical composition comprising a VNAR polypeptide of claim 1 or 4 or a conjugate thereof.

10. A conjugate comprising a heterologous molecule operably linked to a VNAR polypeptide of claim 1.

11. The conjugate of claim 10, wherein said operable linkage is capable of dissociation after endocytosis into, transport into or transport across a cell to thereby release said heterologous molecule into or across said cell.

12. A kit for detecting or quantifying TfR-1 in a sample which comprises at least one VNAR polypeptide of claim 1 or a conjugate thereof.

13. A nucleic acid encoding at least one VNAR polypeptide of claim 1 or a conjugate thereof, wherein said conjugate is a fusion protein with a proteinaceous diagnostic or therapeutic agent operably linked to said polypeptide.

14. A vector comprising a nucleic acid of claim 13.

15. A host cell comprising the vector of claim 14.

16. A method of delivering a therapeutic or diagnostic molecule across the blood brain barrier which comprises administering a conjugate of claim 11 to a subject for a time and in an amount effective to treat or diagnose a CNS disease or condition.

17. A method of delivering a therapeutic or diagnostic molecule to the gastrointestinal (GI) tract which comprises administering a conjugate of claim 11 to a subject for a time and in an amount effective to treat or diagnose a GI disease or condition.

18. A method of identifying, quantifying or localizing a TfR-1-containing biological sample or cell which comprises contacting a test sample in vitro or in vivo with at least one VNAR polypeptides of claim 1, and directly or indirectly measuring the TfR-specific binding in or to said sample.

19. A method of treating a disease or condition which comprises administering to a subject in need thereof a compound or composition comprising a conjugate of claim 11, wherein the disease or condition is ameliorated upon transport of a heterologous molecule across a cell membrane of a TfR-positive cell.

20. The method of claim 19, wherein said VNAR polypeptide is internalized by a TfR in a cell membrane associated with the blood brain barrier or the gastrointestinal (GI) tract.

21. The method of claim 19, wherein the disease or condition is a central nervous system disease or condition, a GI disease or condition or cancer.

22. The method of claim 19, wherein the disease or condition is cancer.

23. The method of claim 22, wherein cancer cells from the subject express a higher level of TfR relative to equivalent non-cancerous cells.

* * * * *